(12) United States Patent
Finkelstein et al.

(10) Patent No.: US 9,402,565 B2
(45) Date of Patent: Aug. 2, 2016

(54) METHOD AND SYSTEM FOR ANALYZING CRANIOFACIAL COMPLEX IMAGES

(71) Applicants: Mor Research Applications Ltd., Tel-Aviv (IL); Ramot at Tel-Aviv University Ltd., Tel-Aviv (IL)

(72) Inventors: Yehuda Finkelstein, Petach-Tikva (IL); Lior Wolf, Herzlia (IL)

(73) Assignees: Mor Research Applications Ltd., Tel-Aviv (IL); Ramot at Tel-Aviv University Ltd., Tel-Aviv (IL)

(*) Notice: Subject to any disclaimer, the term of this patent is extended or adjusted under 35 U.S.C. 154(b) by 0 days.

(21) Appl. No.: 14/874,498

(22) Filed: Oct. 5, 2015

(65) Prior Publication Data

US 2016/0029927 A1   Feb. 4, 2016

Related U.S. Application Data

(63) Continuation of application No. 13/827,111, filed on Mar. 14, 2013, now Pat. No. 9,153,022, which is a continuation-in-part of application No. PCT/IL2011/000737, filed on Sep. 15, 2011.

(60) Provisional application No. 61/383,387, filed on Sep. 16, 2010.

(51) Int. Cl.
*G06K 9/00* (2006.01)
*A61B 5/107* (2006.01)
*G06T 7/00* (2006.01)
*A61B 5/00* (2006.01)
*A61B 5/08* (2006.01)
*G06K 9/46* (2006.01)

(52) U.S. Cl.
CPC .............. *A61B 5/1075* (2013.01); *A61B 5/08* (2013.01); *A61B 5/4818* (2013.01); *G06K 9/46* (2013.01); *G06T 7/0014* (2013.01); *G06T 7/0028* (2013.01); *G06T 2200/04* (2013.01); *G06T 2207/10116* (2013.01); *G06T 2207/30008* (2013.01); *G06T 2207/30036* (2013.01); *G06T 2207/30196* (2013.01)

(58) Field of Classification Search
None
See application file for complete search history.

(56) References Cited

U.S. PATENT DOCUMENTS 6,068,482 A   5/2000   Snow
7,794,399 B2  9/2010   Singh
(Continued)

FOREIGN PATENT DOCUMENTS

WO   WO 2008/000055   1/2008
WO   WO 2009/043080   4/2009
WO   WO 2012/035538   3/2012

OTHER PUBLICATIONS

Communication Pursuant to Article 94(3) EPC Dated May 7, 2014 From the European Patent Office Re. Application No. 11781658.7.
(Continued)

*Primary Examiner* — Wenpeng Chen

(57) ABSTRACT

In a method of analysis, a target image is registered to define a plurality of keypoints arranged in sets corresponding to polygons or linear segments in the target image. A database of registered and annotated images is accessed and a polygon-wise comparison between the target image and each database image is employed. The comparison is used for projecting annotated locations from the database images into the target image.

22 Claims, 26 Drawing Sheets
(19 of 26 Drawing Sheet(s) Filed in Color)

(56) References Cited

U.S. PATENT DOCUMENTS

| | | | |
|---|---|---|---|
| 8,326,086 | B2 | 12/2012 | Carlsen et al. |
| 2002/0154819 | A1 | 10/2002 | Campbell |
| 2003/0052875 | A1 | 3/2003 | Salomie |
| 2003/0194057 | A1 | 10/2003 | Dewaele |
| 2005/0259882 | A1 | 11/2005 | Dewaele |
| 2008/0064008 | A1 | 3/2008 | Schmitt |
| 2008/0205719 | A1 | 8/2008 | Pekar et al. |
| 2009/0198100 | A1 | 8/2009 | Moore |
| 2009/0316966 | A1 | 12/2009 | Marshall et al. |
| 2009/0324100 | A1* | 12/2009 | Kletter ............... G06K 9/00442 382/217 |
| 2011/0244415 | A1 | 10/2011 | Batesole |
| 2011/0268326 | A1 | 11/2011 | Kuo et al. |
| 2012/0022365 | A1 | 1/2012 | Mansfield |
| 2012/0063655 | A1 | 3/2012 | Dean et al. |
| 2013/0094704 | A1 | 4/2013 | Hamadeh et al. |
| 2013/0217996 | A1 | 8/2013 | Finkelstein et al. |

OTHER PUBLICATIONS

International Preliminary Report on Patentability Dated Mar. 28, 2013 From the International Bureau of WIPO Re. Application No. PCT/IL2011/000737.

International Search Report and the Written Opinion Dated Feb. 7, 2012 From the International Searching Authority Re. Application No. PCT/IL2011/000737.

Official Action Dated Feb. 18, 2015 From the US Patent and Trademark Office Re. U.S. Appl. No. 13/827,111.

Battagel et al. "A Cephalometric Comparison of Subjects With Snoring and Obstructive Sleep Apnoea", European Journal of Orthodontics, 22: 353-365, 2000.

Battagel et al. "Changes in Airway and Hyoid Position in Response to Mandibular Protrusion in Subjects With Obstructive Sleep Apnoea (OSA)", European Journal of Orthodontics 21: 363-376, 1999.

Celik et al. "Comparison of Cephalometric Measurements With Digital Versus Conventional Cephalometric analysis", European Journal of Orthodontics, Advance Access, p. 1-6, Feb. 23, 2009.

Chen et al. "Automatically Conflating Road Vector Data With Orthoimagery", Geoinformatica, XP019465231, 10(4): 495-530, Jan. 13, 2007. p. 498-500, p. 503, p. 507, p. 509, Figs.2, 6, 9, 11, 12-14.

Cheng "Mean Shift, Mode Seeking, and Clustering", IEEE Transactions on Pattern Analysis and Machine Intelligence, 17(8): 790-799, Aug. 1995.

Cootes et al. "Active Appearance Models", IEEE Transactions on Pattern Analysis and Machine Intelligence, 23(6): 681-685, Jun. 2001.

Dalal et al. "Histograms of Oriented Gradients for Human Detection", Proceedings of the 2005 IEEE Computer Society Conference on Computer Vision and Pattern Recognition (CVPR'05), p. 1063-1069, 2005.

Finkelstein et al. "Frontal and Lateral Cephalometry in Patients With Sleep-Disordered Breathing", The Laryngoscope, 111: 634-641, Apr. 2001.

Fleisher et al. "Current Trends in the Treatment of Obstructive Sleep Apnea", Journal of Oral and Maxillofacial Surgeons, 65: 2056-2068, 2007.

Grybauskas et al. "Validity and Reproducibility of Cephalometric Measurements Obtained From Digital Photographs of Analogue Headfilms", Stomatologija, Baltic Dental and Maxillofacial Journal, 9(4): 114-120, 2007.

Hammond et al. "A Follow-Up Study of Dental and Skeletal Changes Associated With Mandibular Advancement Splint Use in Obstructive Sleep Apnea", American Journal of Orthodontics and Dentofacila Orthopedics, 132(6): 806-814, Dec. 2007.

Hoekema et al. "Craniofacial Morphology and Obstructive Sleep Apnoea: A Cephalometric Analysis", Journal of Oral Rehabilitation, 30: 690-696, 2003.

Hutton et al. "An Evaluation of Active Shape Models for the Automatic Identification of Cephalometric Landmarks", European Journal of Orthodontics, 22: 499-508, 2000.

Kafieh et al. "Automatic Landmark Detection in Cephalometry Using a Modified Active Shape Model With Sub Image Matching", IEEE International Conference on Machine Vision, ICMV 2007, Islamabad, Pakistan, Dec. 28-29, 2007, XP031237819, p. 73-78, Dec. 28, 2007. p. 76, Fig.4.

Ke et al. "PCA-SIFT: A More Distinctive Representation for Local Image Descriptors", Proceedings of the 2004 IEEE Computer Society Conference on Computer Vision and Pattern Recognition, Washington DC, USA, Jun. 27-Jul. 2. 2004, 2: II-506-II-513, Jul. 19, 2004.

Kim et al. "Pharyngeal Airway Changes After Sagittal Split Ramus Osteotomy of the Mandible: A Comparison Between Genders", Journal of Oral and Maxillofacial Surgeons, 68: 1802-1806, 2010.

Kollias et al. "Adult Craniocervical and Pharyngeal Changes—A Longitudinal Cephalometric Study Between 22 and 42 Years of Age. Part I: Morphological Craniocervical and Hyoid Bone Changes", European Journal of Orthodontics, 21: 333-344, 1999.

Maltais et al. "Cephalometric Measurements in Snorers, Non-Snorers, and Patients With Sleep Apnoea", Thorax, 46: 419-423, 1991.

Mayer et al. "Relationship Between Body Mass Index, Age and Upper Airway Measurements in Snorers and Sleep Apnoea Patients", European Respiratory Journal, 9: 1801-1809, 1996.

Mikolajczyk et al. "A Performance Evaluation of Local Descriptors", IEEE Transactions on Pattern Analysis and Machine Intelligence, 27(10): 1615-1630, Oct. 2005.

Obdrzalek et al. "Object Recognition Using Local Affine Frames on Distinguished Regions", British Machine Vision Conference, BMVC 2002, 113-122, 2002.

Rueda et al. "An Approach for the Automatic Cephalometric Landmark Detection Using Mathematical Morphology and Active Appearance Models", International Conference on Medical Image Computing and Computer-Assisted Intervention: MICCAI 2006, LNCS 4190, 9(Pt.1): 159-166, 2006.

Sakakibara et al. "Cephalometric Abnormalities in Non-Obese and Obese Patients With Obstructive Sleep Apnoea", European Respiratory Journal, 13: 403-410, 1999.

Wolf et al. "Automatic Cephalometric Evaluation of Patients Suffering From Sleep-Disordered Breathing", Medical Image Computing and Computer-Assisted Intervention A, MICCAI 2010, XP019151850, Part III, LNCS 6363: 642-649, Sep. 20, 2010.

Yue et al. "Automated 2-D Cephalometric Analysis on X-Ray Images by A Model-Based Approach", IEEE Transactions on Biomedical Engineering, XP002468556, 53(8): 1615-1623, Aug. 1, 2006. p. 1-5, Figs.3, 4, 6.

\* cited by examiner

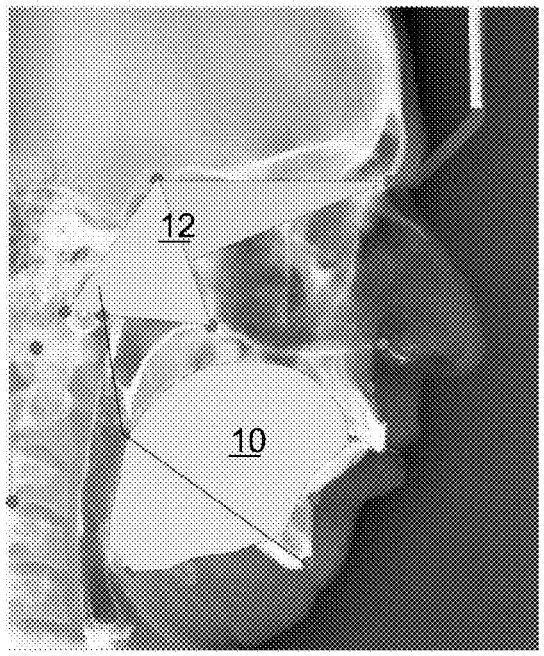
FIG. 1A
FIG. 1B
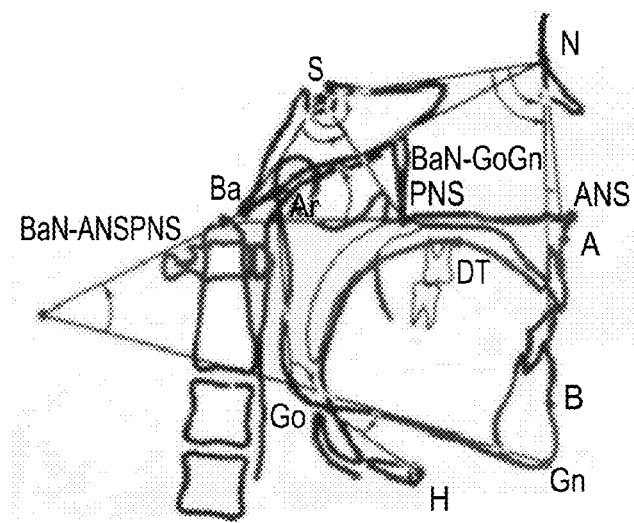
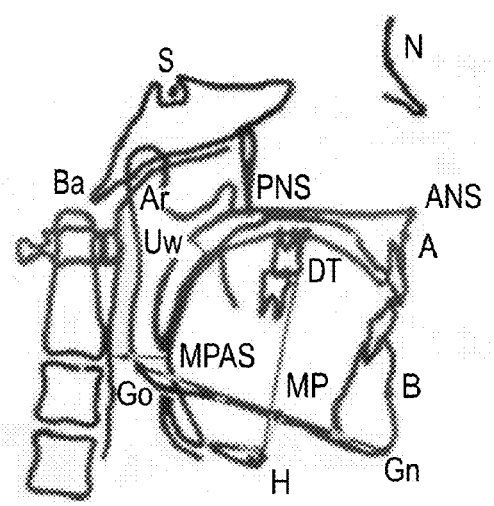
FIG. 1C
FIG. 1D

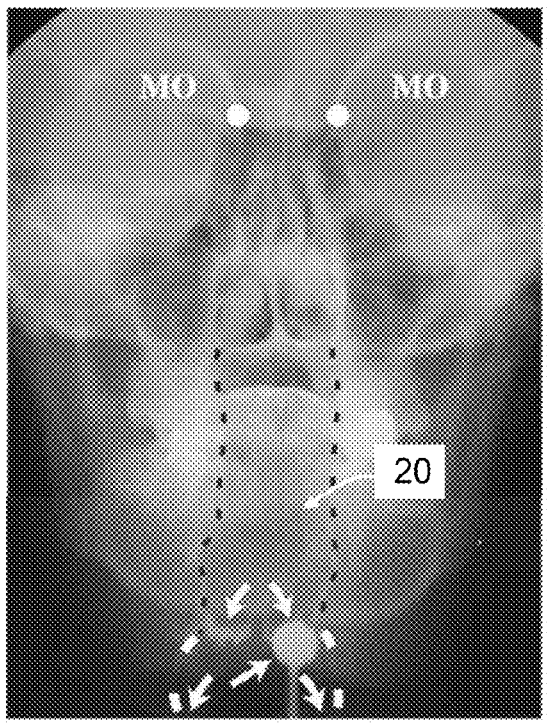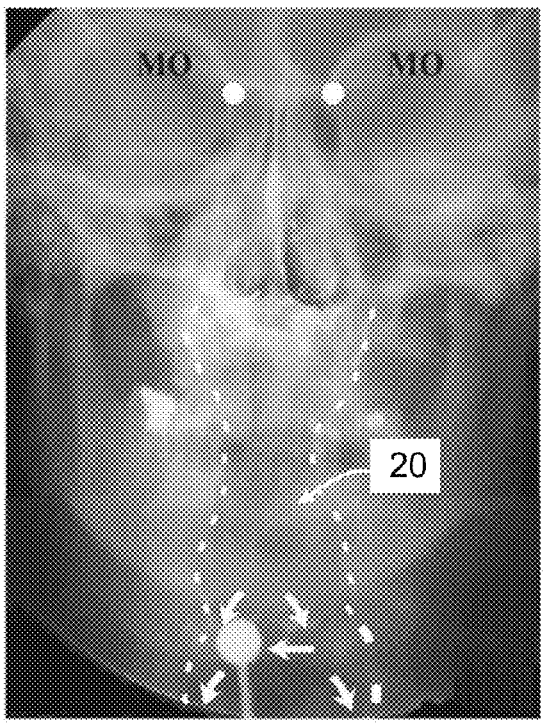
FIG. 2A    FIG. 2B
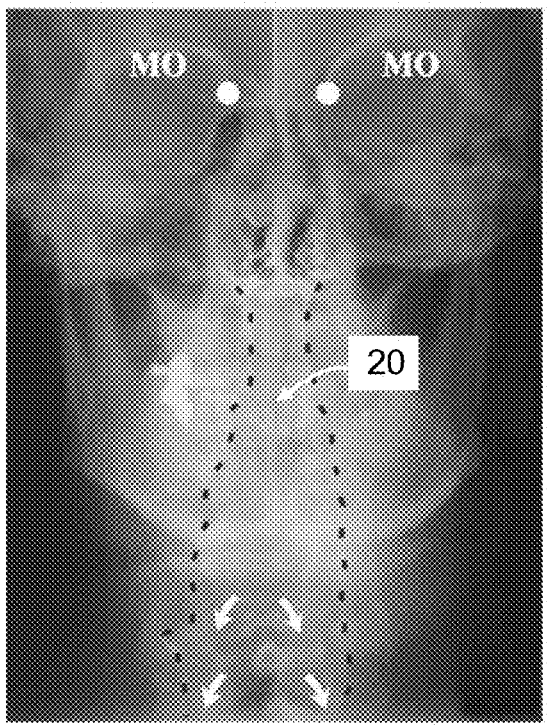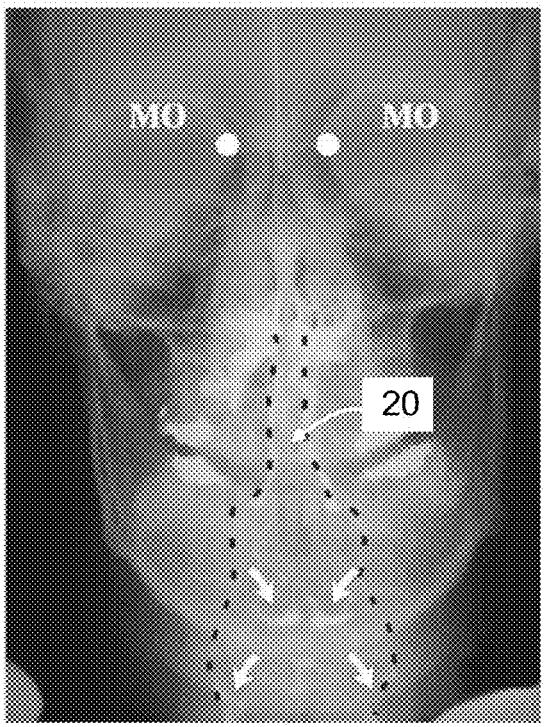
FIG. 2C    FIG. 2D

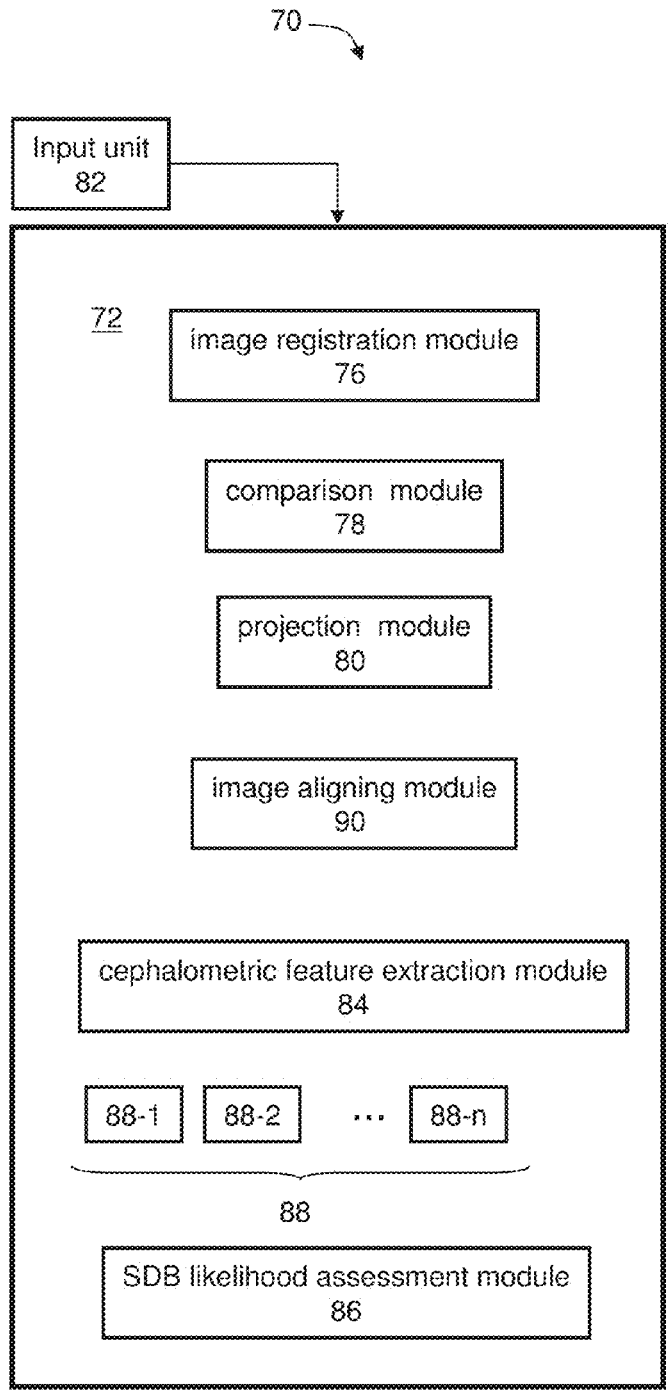
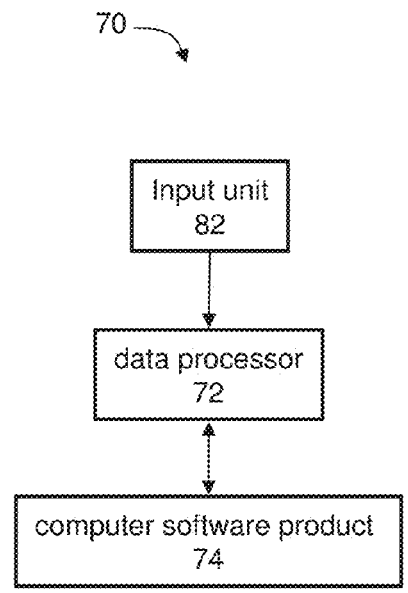
FIG. 7B
FIG. 7A

FIG. 11A
FIG. 11B
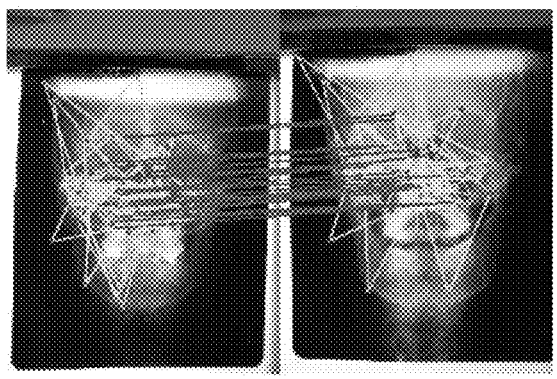
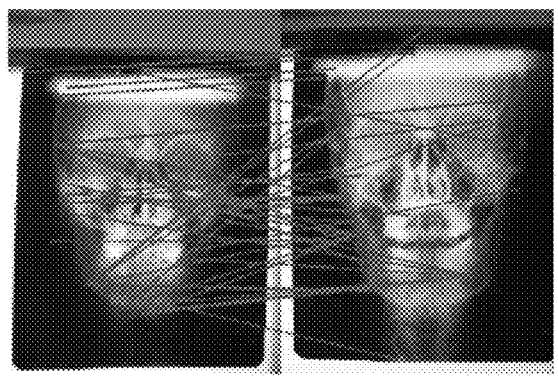
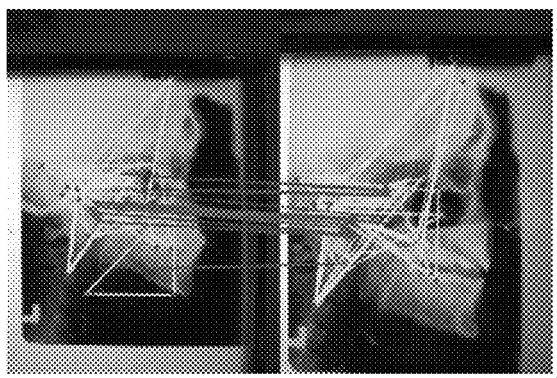
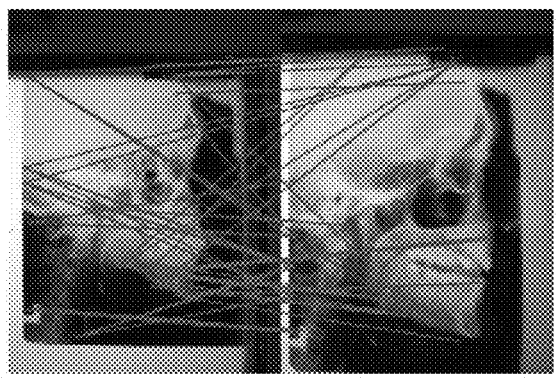
FIG. 11C
FIG. 11D

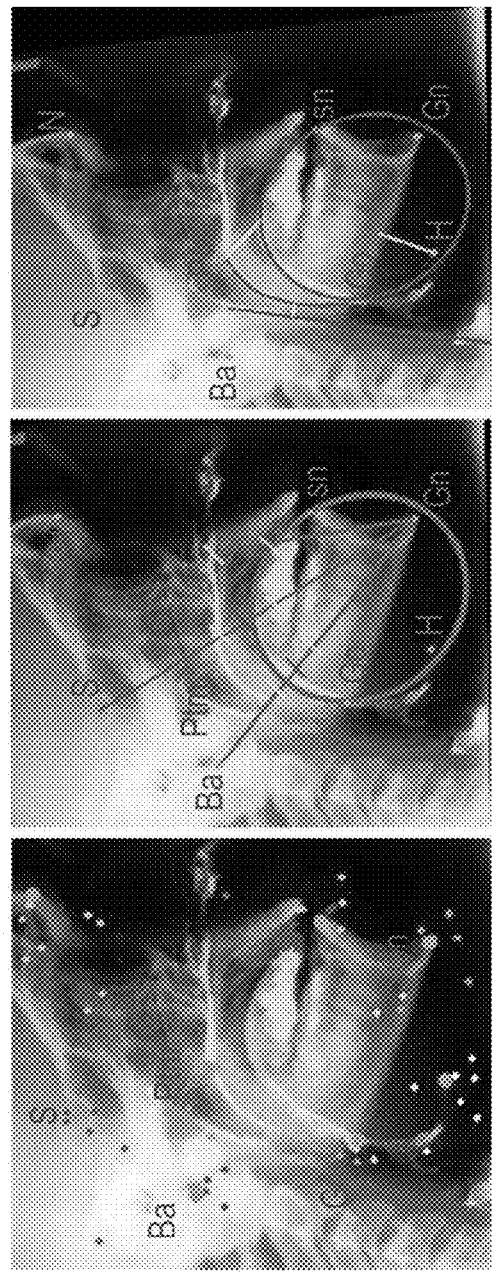

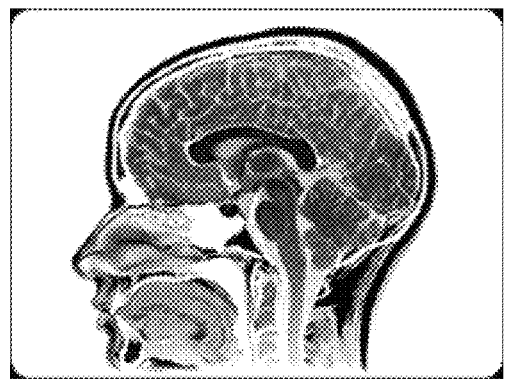
FIG. 22
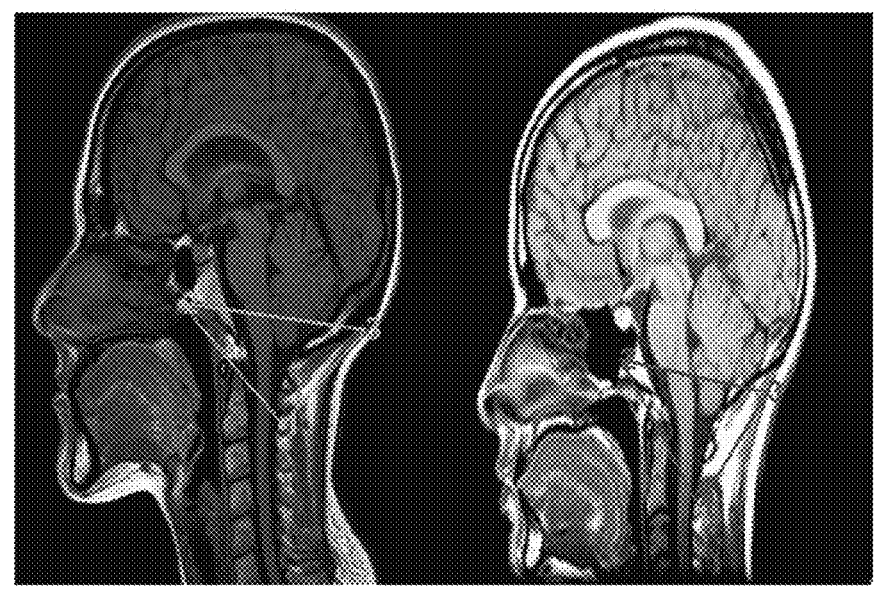
FIG. 23A          FIG. 23B
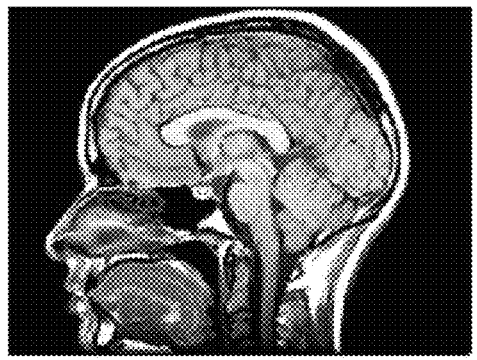    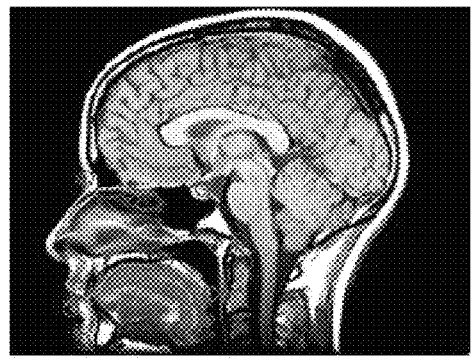
FIG. 24A          FIG. 24B

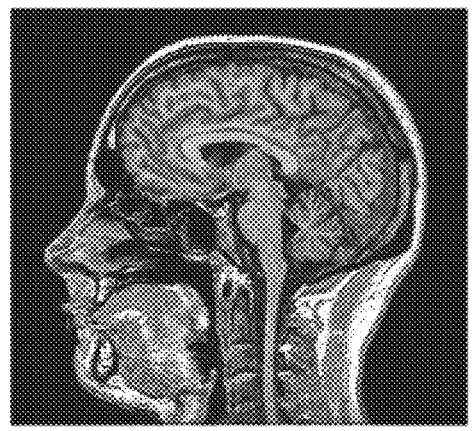
FIG. 25
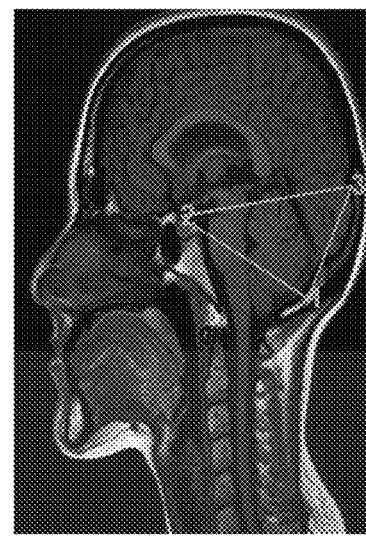 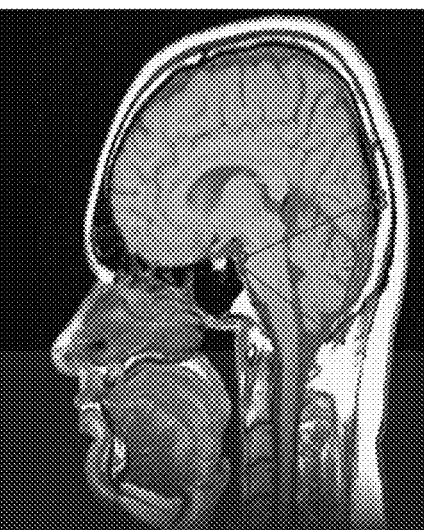
FIG. 26A FIG. 26B
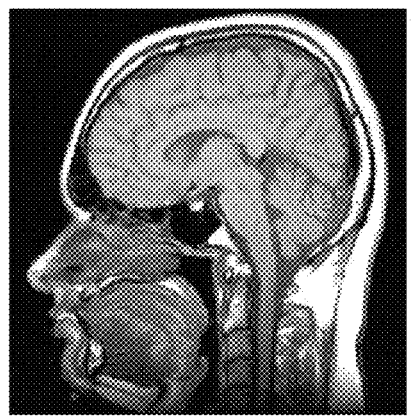 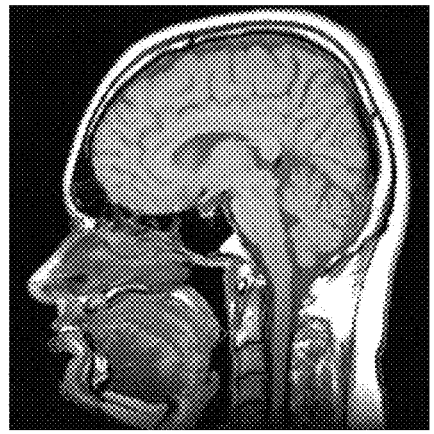
FIG. 27A FIG. 27B

METHOD AND SYSTEM FOR ANALYZING CRANIOFACIAL COMPLEX IMAGES

RELATED APPLICATION

This application is a continuation of U.S. patent application Ser. No. 13/827,111 filed on Mar. 14, 2013, which is a Continuation-in-Part of PCT Patent Application No. PCT/IL2011/000737 filed on Sep. 15, 2011, which claims the benefit of priority of U.S. Provisional Patent Application No. 61/383,387, filed on Sep. 16, 2010. The contents of the above applications are all incorporated by reference as if fully set forth herein in their entirety.

FIELD AND BACKGROUND OF THE INVENTION

The present invention, in some embodiments thereof, relates to image analysis and, more particularly, but not exclusively, to a method and system for cephalometric analysis.

Medical practitioners, such as orthodontists, maxillofacial surgeons, ear, nose and throat surgeons, and other physicians use cephalometry for diagnosis, prognosis and treatment planning. Cephalometric analysis allows defining certain norms and anomalies of a skeletal, dental and soft tissue of the craniofacial complex. Cephalometric measures of individuals can be compared with norms for age, sex and population group. Generally, cephalometric analysis includes identification of specific landmarks on a roentgenogram (an X-ray image) of the head. By plotting lines on the image, and measuring various measures of these lines the medical practitioner evaluates growth and development of anatomic structures. A comparison of the measures to previously acquired control group measures (e.g., normal populations of similar age, gender and ethnic group) allows the practitioner to diagnose bony and soft tissue anatomical variants and anomalies.

Cephalometric analysis has also been proposed as a tool for diagnosing sleep-disordered breathing (SDB) [Finkelstein et al., "Frontal and lateral cephalometry in patients with sleep-disordered breathing," The Laryngoscope 111, 4:623-641 (2001)]. Lateral and frontal cephalometric radiographs were analyzed in a series of normal patients and those with varying degrees of SDB, and the degrees of narrowing or other unfavorable anatomical changes that may differentiate SDB subjects from normal subjects. SDB was found to be associated with statistically significant changes in several cephalometric measurements.

Additional background art includes Hoekema et al., "Craniofacial morphology and obstructive sleep apnoea: a cephalometric analysis," J Oral Rehabil., 2003, 30(7):690-696; Maltais et al., "Cephalometric measurements in snorers, non-snorers, and patients with sleep apnea," Thorax, 1991, 46: 419-423; Sakakibara et al., "Cephalometric abnormalities in non-obese and obese patients with obstructive sleep apnoea," Eur Respir J, 1999, 13:403-410; Mayer et al., "Relationship between body mass index, age and upper airway measurements in snorers and sleep apnea patients," Eur Respir J, 1996, 9, 1801-1809; Fleisher et al., "Current Trends in the Treatment of Obstructive Sleep Apnea," J Oral Maxillofac Surg 65:2056-2068, 2007; Battagel et al., "A cephalometric comparison of subjects with snoring and obstructive sleep apnea," European Journal of Orthodontics 22, 2000, 353-365; Battagel et al., "Changes in airway and hyoid position in response to mandibular protrusion in subjects with obstructive sleep apnoea (OSA)," Eur J Orthod, 1999, 21 (4): 363-376; Hammond et al., "A follow-up study of dental and skeletal changes associated with mandibular advancement splint use in obstructive sleep apnea," American Journal of Orthodontics and Dentofacial Orthopedics, Volume 132, 2007; Grybauskas et al., "Validity and reproducibility of cephalometric measurements obtained from digital photographs of analogue headfilms," Stomatologija, Baltic Dental and Maxillofacial Journal, 9:114-120, 2007; Celik et al., "Comparison of cephalometric measurements with digital versus conventional cephalometric analysis," Eur J Orthod, 2009, 31 (3): 241-246; Kim et al., "Pharyngeal airway changes after sagittal split ramus osteotomy of the mandible: a comparison between genders," J Oral Maxillofac Surg., 2010, 68(8):1802-6; Kollias et al., "Adult craniocervical and pharyngeal changes—a longitudinal cephalometric study between 22 and 42 years of age. Part I: Morphological craniocervical and hyoid bone changes," European Journal of Orthodontics, 1999, 21(4):333-344; Cootes et al., "Active appearance models," Pattern Analysis and Machine Intelligence, IEEE Transactions on 23(6), 2001, 681-685; Hutton et al., "An evaluation of active shape models for the automatic identification of cephalometric landmarks," Eur. J. Orthodont, 22, 2000; Kafieh et al., "Automatic landmark detection in cephalometry using a modified active shape model with sub image matching," ICMV07, 2007, 73-78, Rueda et al., "An approach for the automatic cephalometric landmark detection using mathematical morphology and AAM," MICCAI, 2006, 159-166; and Yue et al., "Automated 2-d cephalometric analysis on x-ray images by a model-based approach," IEEE. Tran. Biomed. Eng. 53(8), 2006.

SUMMARY OF THE INVENTION

According to an aspect of some embodiments of the present invention there is provided a method of analysis. The method comprises: registering a target image to define a plurality of keypoints arranged in sets corresponding to polygons or linear segments in the target image; accessing a database of registered and annotated images, and employing a polygon-wise comparison between the target image and each database image; and using the comparison for projecting annotated locations from the database images into the target image.

According to some embodiments of the invention the target image is an image of the craniofacial complex of a subject, wherein the annotated locations correspond to cephalometric landmarks and wherein the method further comprises extracting cephalometric features from the target image based on the annotated locations.

According to some embodiments of the invention the invention the method comprises repeating the analysis for an additional target image of the craniofacial complex of the same subject, wherein the target image and the additional target image correspond to different viewpoints.

According to some embodiments of the invention the extraction of the cephalometric features comprises identifying three-dimensional cephalometric structures based on the different viewpoints.

According to some embodiments of the invention the cephalometric features comprise angular relations between the cephalometric landmarks.

According to some embodiments of the invention the angular relations comprise at least one angle selected from the group consisting of a skull base angle, a bony nasopharyngeal angle, a mandibular plane hyoid angle, and a skull base orientation angle between a the Basion-Pterygomaxillare line and the Basion-Sella line.

According to some embodiments of the invention the extraction of the cephalometric features comprises modeling a shape of at least one cephalometric structure and fitting the model to annotated locations corresponding to the cephalometric structure in the target image.

According to some embodiments of the invention the at least one cephalometric structure is the tongue, and the modeling comprises modeling the tongue as an ellipse.

According to some embodiments of the invention the at least one cephalometric structure is the velum, and the modeling comprises modeling the velum using a basis spline.

According to some embodiments of the invention the at least one cephalometric structure is the pharyngeal wall, and the modeling comprises modeling the pharyngeal wall as a straight line.

According to some embodiments of the invention the method comprises assessing sleep disordered breathing (SDB) and/or the likelihood of SDB of the subject, based, at least in part, on the cephalometric features.

According to some embodiments of the invention the method comprises calculating a respiratory disturbance index of the subject, based, at least in part, on the cephalometric features.

According to some embodiments of the invention the method comprises calculating characteristic pharyngeal airflow resistance, based, at least in part, on the cephalometric features.

According to some embodiments of the invention the method comprises assessing the SDB or likelihood of SDB of the subject, based, at least in part, on the three-dimensional cephalometric structures.

According to some embodiments of the invention the method comprises calculating a respiratory disturbance index of the subject, based, at least in part, on the three-dimensional cephalometric structures.

According to some embodiments of the invention the target image is an image of the craniofacial complex of the subject before a treatment, and the method comprises repeating the analysis for at least one additional target image of the craniofacial complex of the same subject but after or during a treatment.

According to some embodiments of the invention the method comprises comparing cephalometric features as extracted from the target image to cephalometric features as extracted from at least one additional target image, and using the comparison for estimating treatment efficiency.

According to some embodiments of the invention the target image is an image of the craniofacial complex of the subject without a dental device, and the method comprises repeating the analysis for an additional target image of the craniofacial complex of the same subject with a dental device.

According to some embodiments of the invention the method comprises comparing cephalometric features as extracted from the target image to cephalometric features as extracted from at least one additional target image, and using the comparison for assessing the effect of the dental device.

According to an aspect of some embodiments of the present invention there is provided a method of assessing SDB or the likelihood of SDB of a subject. The method comprises: analyzing a target image of the craniofacial complex of the subject to identify shapes of cephalometric structures in the image; classifying the shapes according to predetermined baseline shapes; assessing SDB or likelihood of SDB responsively to the classification; and issuing a report pertaining to the assessment.

According to some embodiments of the invention the method comprises repeating the identification and the classification for an additional target image corresponding to a different viewpoint of the craniofacial complex of the same subject, wherein the assessment is based on both the classifications.

According to some embodiments of the invention the method comprises receiving non-cephalometric information, wherein the SDB or likelihood of SDB is assessed also responsively to the non-cephalometric information.

According to some embodiments of the invention the non-cephalometric information comprises information pertaining to at least one of: nasal obstruction, glottic narrowing, adherent velum, pharyngeal collapse, epiglottic collapse and edema of posterior larynx.

According to some embodiments of the invention the non-cephalometric information comprises Body Mass Index.

According to some embodiments of the invention the sets comprise equal number of keypoints.

According to some embodiments of the invention each of the sets is a triplet of keypoints corresponding to a triangle.

According to some embodiments of the invention the registration comprises, for each set of keypoints, employing an affine transformation to the set for mapping the set to a predetermined set of coordinates.

According to some embodiments of the invention the method extracts for each set of keypoints, a histogram of edge directions from the set.

According to some embodiments of the invention the method further comprises aligning the target image and the database image according to the annotated cephalometric landmarks.

According to some embodiments of the invention the plurality of keypoints are defined using a Scale-Invariant Feature Transform (SIFT) algorithm featuring a Difference of Gaussian (DoG) operator.

According to an aspect of some embodiments of the present invention there is provided a system for analyzing an image. The system comprises a data processor configured for receiving the image, and executing the method as described herein.

According to an aspect of some embodiments of the present invention there is provided a computer software product. The computer software product comprises a computer-readable medium in which program instructions are stored, which instructions, when read by a data processor, cause the data processor to receive an image and execute the method as described herein.

According to some embodiments of the invention target image is an X-ray image.

According to some embodiments of the invention the target image is a Computerized Tomography (CT) image.

According to some embodiments of the invention the target image is a Magnetic Resonance (MR) image.

According to some embodiments of the invention the target image is sliced image having a set of image slices and the method comprises transferring annotated locations among different image slices of the set.

According to some embodiments of the invention the target image is a three-dimensional image, wherein the annotated locations are projected the said three-dimensional image in a three-dimensional manner.

According to some embodiments of the invention the target image is selected from the group consisting of a thermal image, an ultraviolet image, a positron emission tomography (PET) image, an ultrasound image, an Electrical Impedance Tomography (EIT) image and a single photon emission computed tomography (SPECT) image.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE SEVERAL VIEWS OF THE DRAWING(S)

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings and images. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 1A-B shows a representative example of analysis of a lateral view image of the craniofacial complex, according to some embodiments of the present invention;

FIGS. 1C-D is a schematic illustration of some craniofacial landmarks which can be used according to some embodiments of the present invention;

FIGS. 2A-F shows a representative example of analysis of frontal view images of the craniofacial complex, according to some embodiments of the present invention;

FIGS. 3A-C are schematic illustrations of a set of linear measures for classifying a pharynx, according to some embodiments of the present invention;

FIG. 4 is a flowchart diagram describing a method suitable for analyzing a target image, according to some embodiments of the present invention;

FIGS. 5A-B show representative examples of annotated cephalometric landmarks, measures and structures suitable for some embodiments of the present invention;

FIG. 6 is a flowchart diagram describing an image registration method, according to some embodiments of the present invention;

FIGS. 7A-B are schematic illustrations of a system for analyzing an image, according to some embodiments of the present invention;

FIGS. 8A-C show an example of cephalometric feature extraction, as performed according to some embodiments of the present invention for a subject that can be assessed as likely to have sleep disordered breathing;

FIGS. 9A and 9B show an example of cephalometric feature extraction, as performed according to some embodiments of the present invention for a subject that can be assessed as having normal breathing during sleep, or very low likelihood of sleep disordered breathing;

FIGS. 10A-H show angular measures between cephalometric features associated with the base of the skull, according to some embodiments of the present invention;

FIGS. 11A-D show results of DoG based imaging matching and triplet-based imaging matching, according to some embodiments of the present invention;

FIGS. 12A-C show a process of anatomical structures fitting, according to some embodiments of the present invention;

Figure 14:
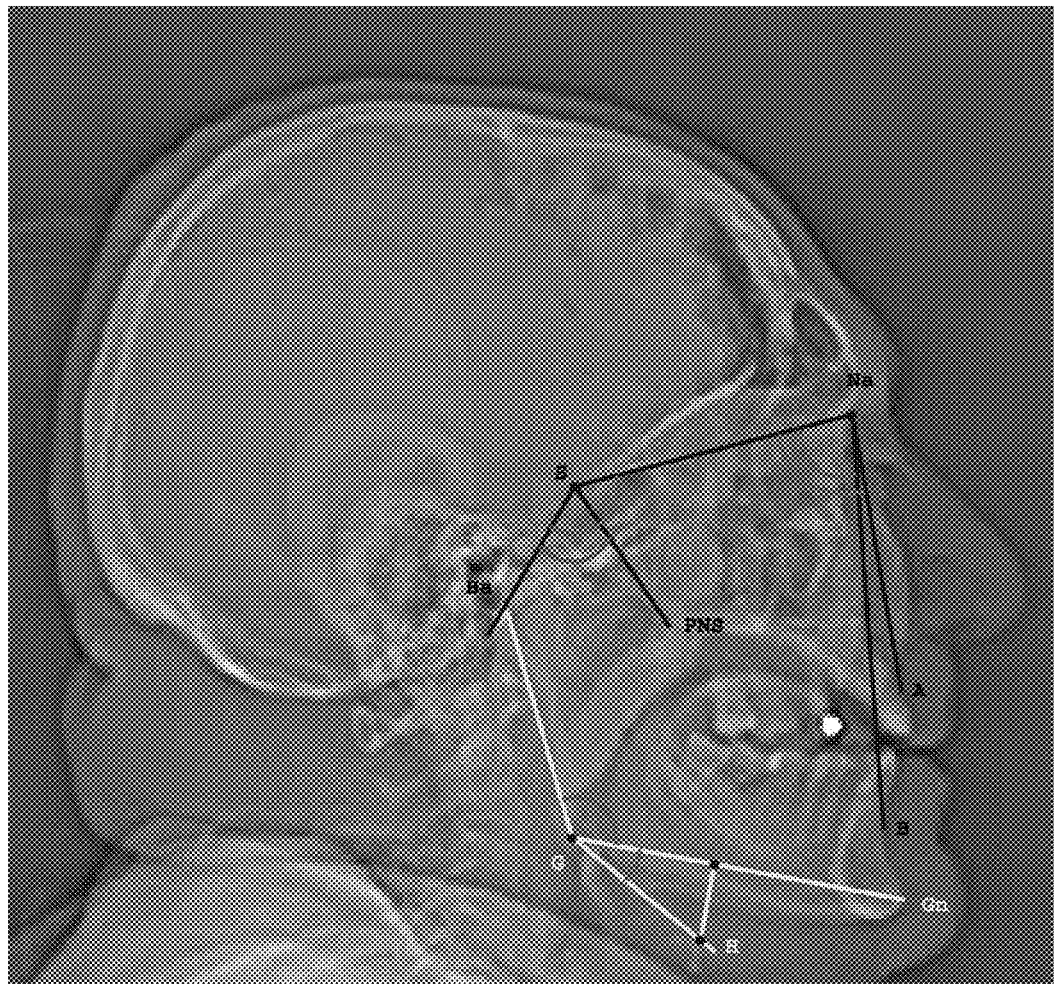
FIG. 14 shows a registered and annotated CT image which was used as a database image according to some embodiments of the present invention.
Figures 16A, 16B:
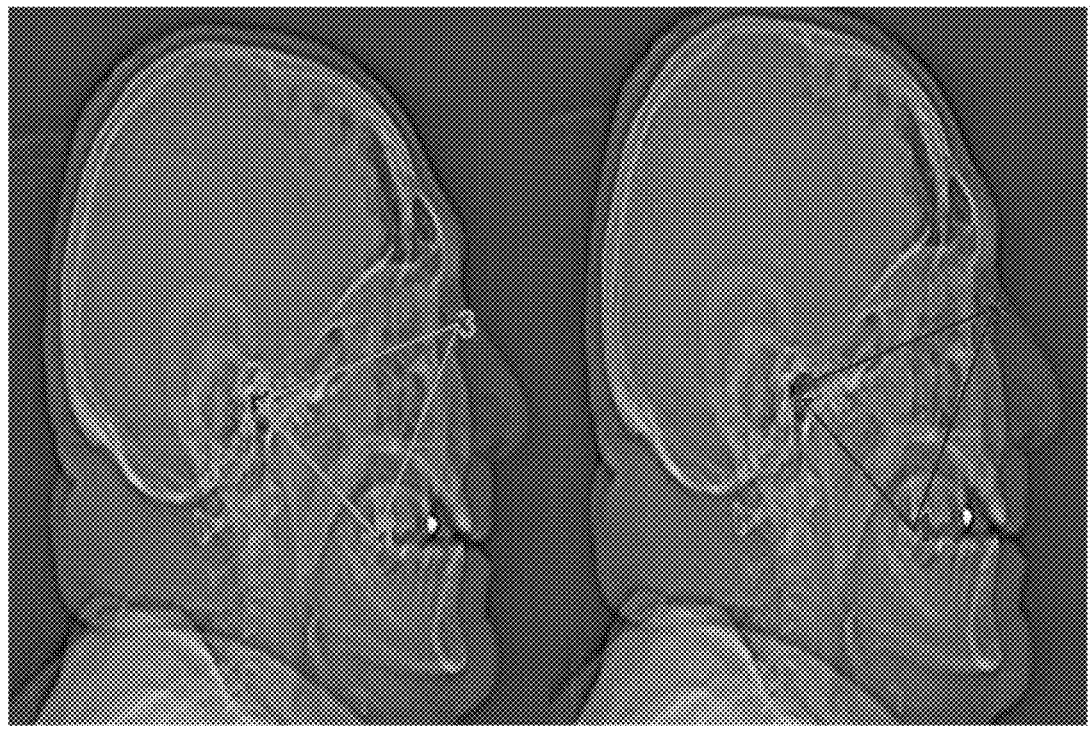
Figure 17:
Figure 18A:
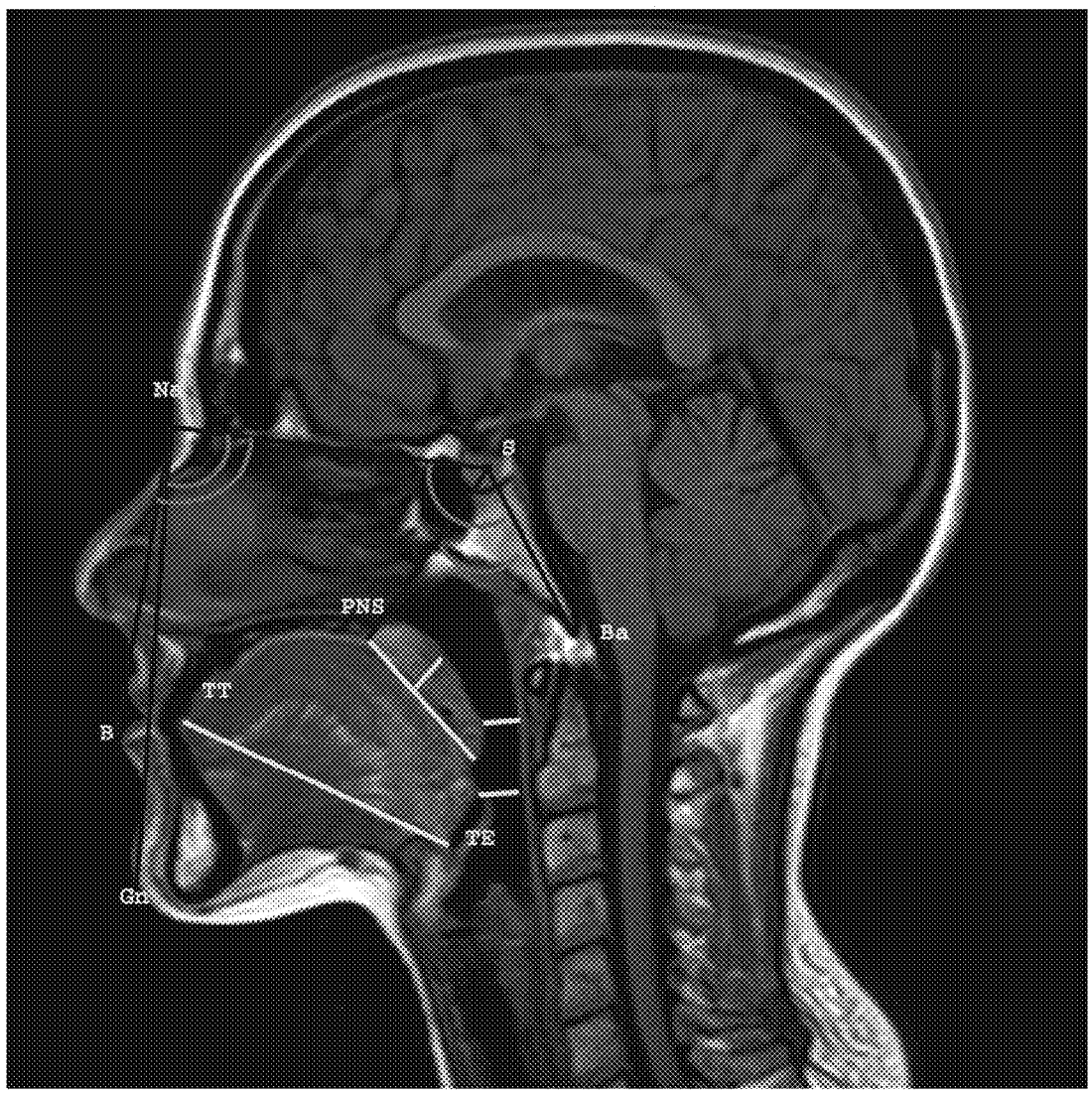
Figure 18B:
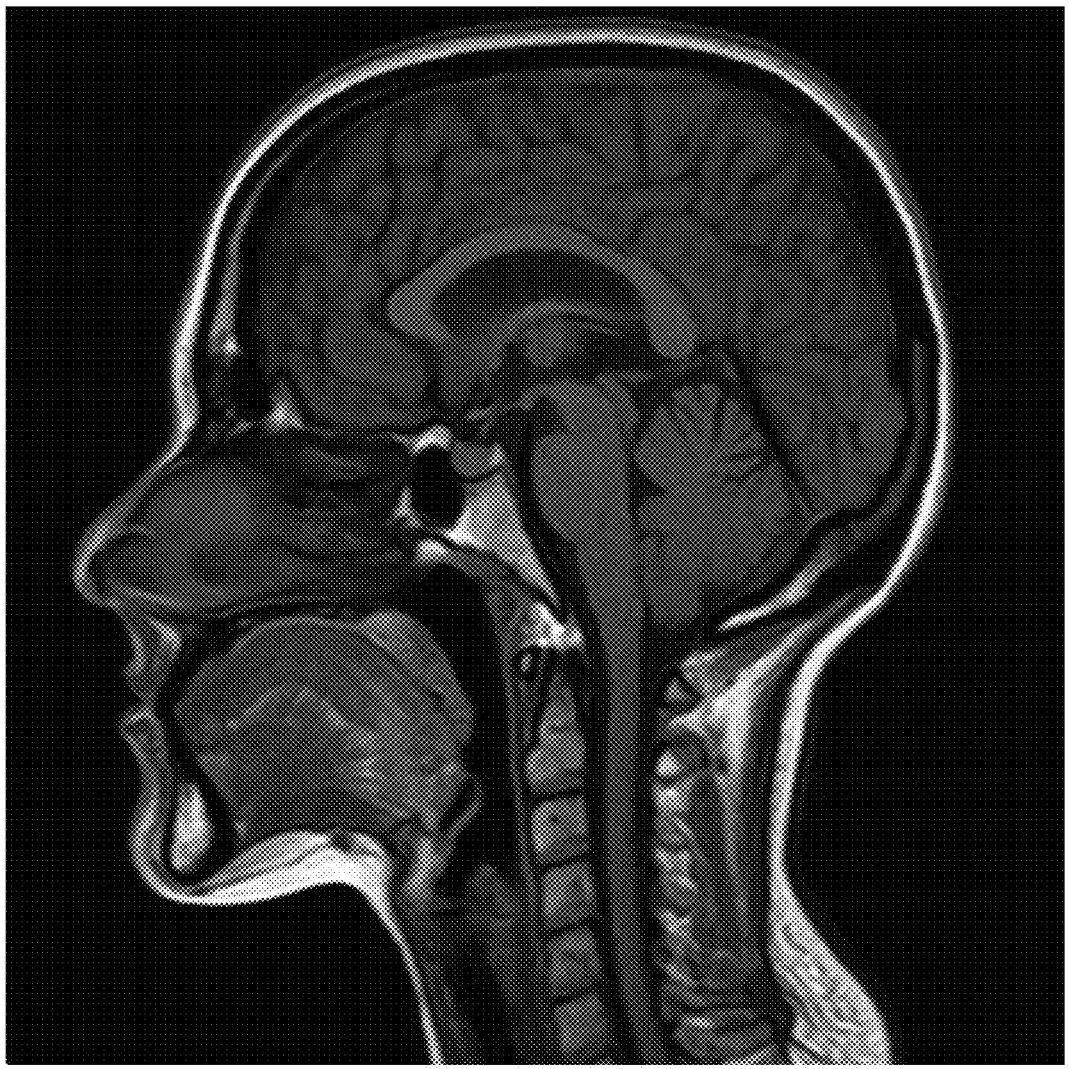
Figure 19:
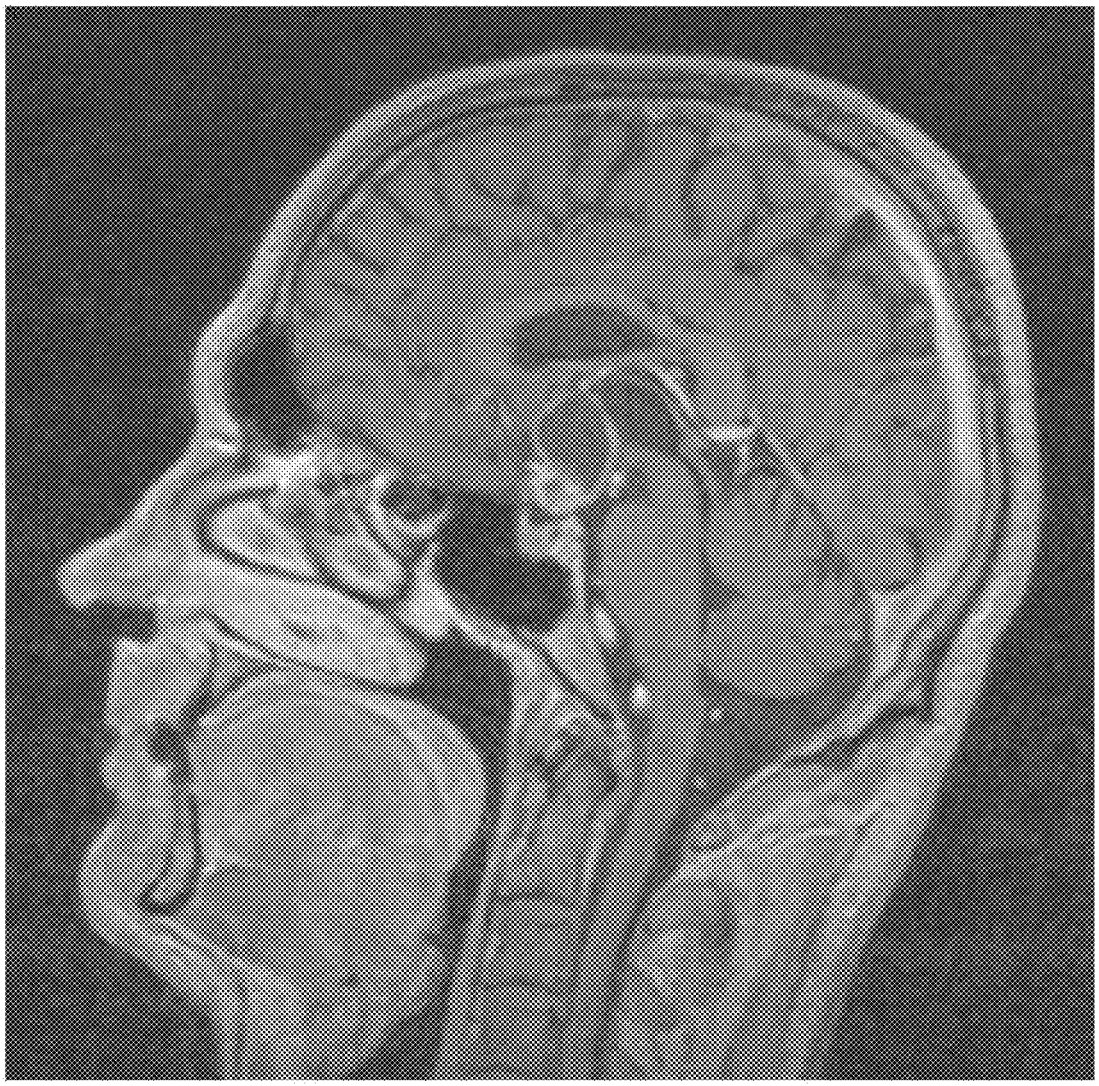
Figures 20A, 20B:
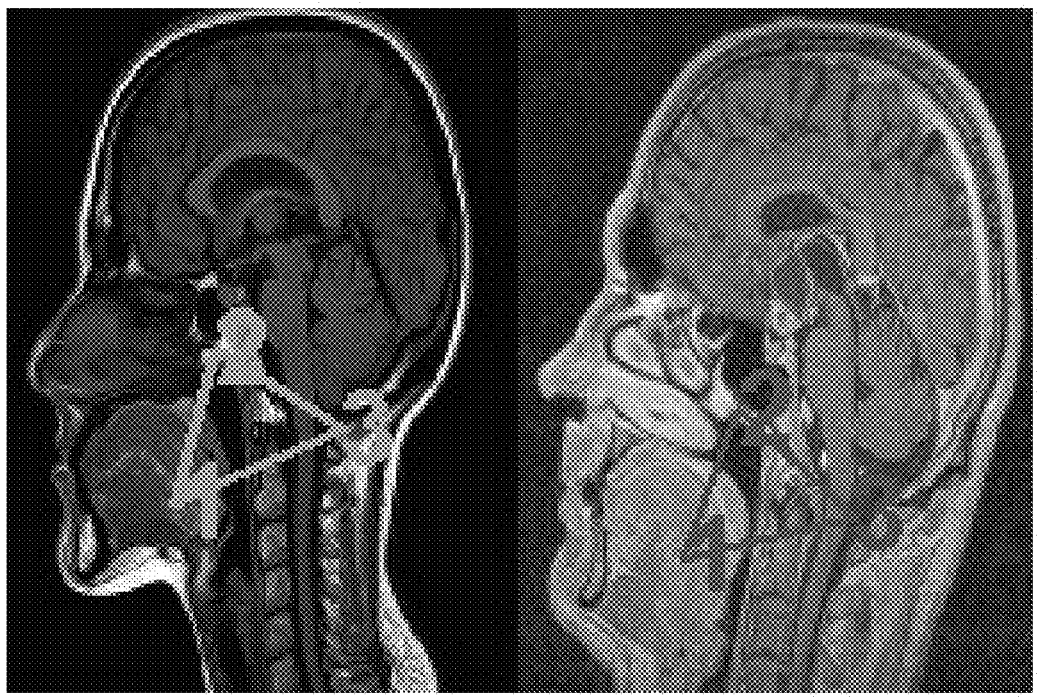
Figure 21A:
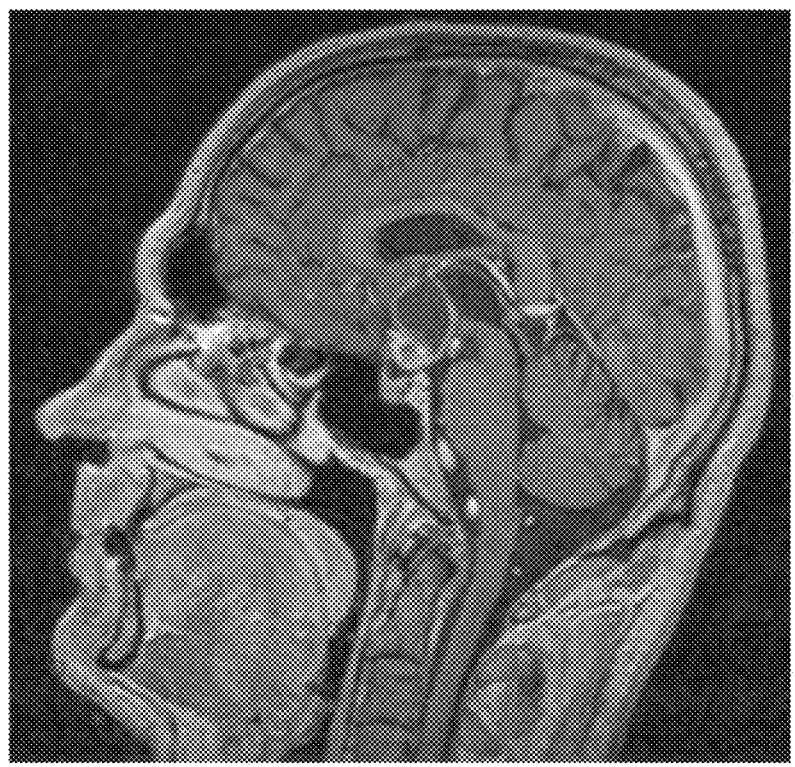
Figure 21B:
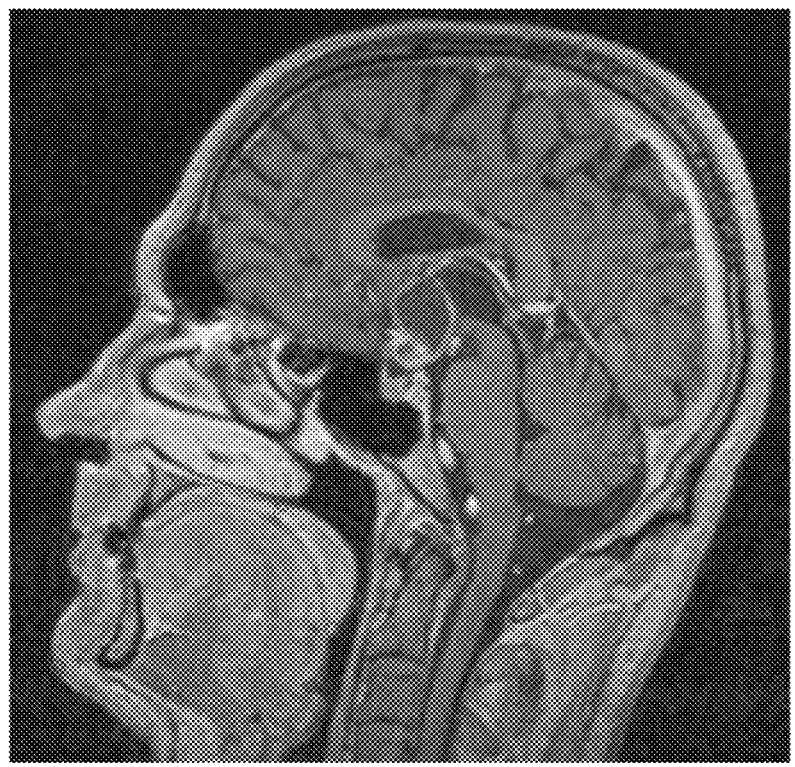

FIGS. 16A-B show a triplet matching between the database image of FIG. 14 and the first target CT image, according to some embodiments of the present invention;

FIG. 17 shows the first target CT image once automatically detected points (red asterisks) were projected onto the image;

FIG. 18A shows a registered and annotated MR image which was used as a database image according to some embodiments of the present invention;

FIG. 18B shows the same MR image as in FIG. 18A, except without the annotation;

FIG. 19 shows a first target MR image which was analyzed according to some embodiments of the present invention;

FIGS. 20A-B show a triplet matching between the database MR image of FIG. 18A and the first target MR image, as obtained according to some embodiments of the present invention;

FIGS. 21A-B show the first target MR image once the points (red asterisks) as automatically detected initially (FIG. 21A) and following an automatic fine-tuning procedure (FIG. 21B) were projected onto the image, according to some embodiments of the present invention;

FIG. 22 shows a second target MR image which was analyzed according to some embodiments of the present invention;

FIGS. 23A-B show a triplet matching between the database MR image of FIG. 18A and the second target MR image, as obtained according to some embodiments of the present invention;

FIGS. 24A-B show the second target MR image once the points (red asterisks) as automatically detected initially (FIG.

Figure 28:
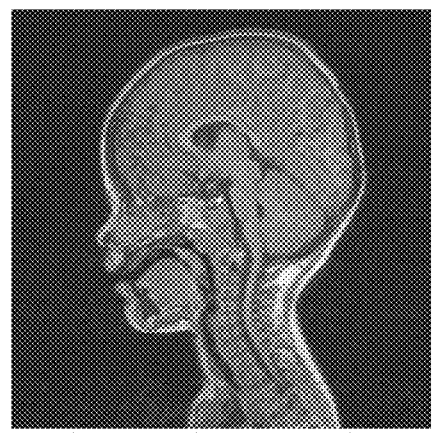
Figures 29A, 29B:
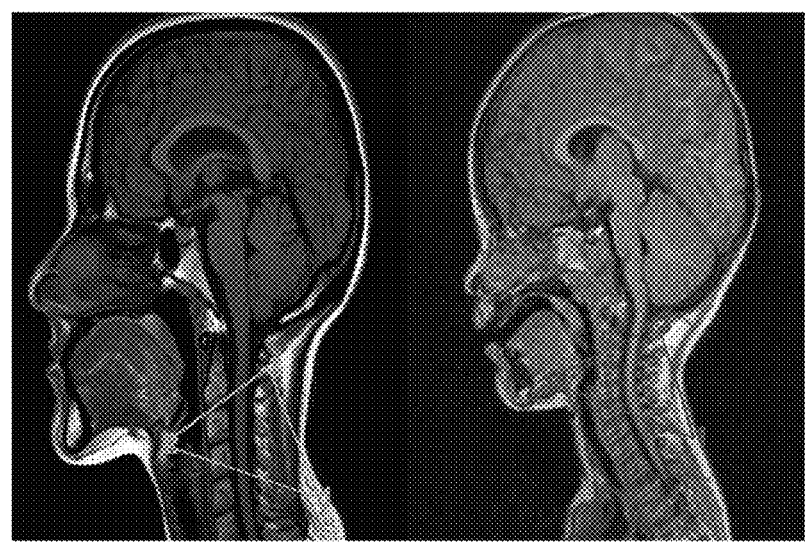
Figure 30:
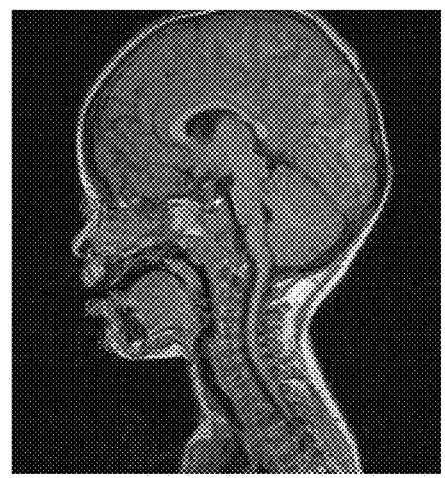

24A) and following an automatic fine-tuning procedure (FIG. 24B) were projected onto the image, according to some embodiments of the present invention;

FIG. 25 shows a third target MR image which was analyzed according to some embodiments of the present invention;

FIGS. 26A-B show a triplet matching between the database MR image of FIG. 18A and the third target MR image (FIG. 26B), as obtained according to some embodiments of the present invention;

FIGS. 27A-B show the third target MR image once the points (red asterisks) as automatically detected initially (FIG. 27A) and following an automatic fine-tuning procedure (FIG. 27B) were projected onto the image, according to some embodiments of the present invention;

FIG. 28 shows a fourth target MR image which was analyzed according to some embodiments of the present invention;

FIGS. 29A-B show a triplet matching between the database MR image of FIG. 18A and the fourth target MR image (FIG. 29B), as obtained according to some embodiments of the present invention; and FIG. 30 shows the fourth target MR image once the points (red asterisks) as automatically detected, following an automatic fine-tuning procedure, were projected onto the image, according to some embodiments of the present invention.

DESCRIPTION OF SPECIFIC EMBODIMENTS OF THE INVENTION

The present invention, in some embodiments thereof, relates to image analysis and, more particularly, but not exclusively, to a method and system for cephalometric analysis.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

The present embodiments are concerned with method and system for analyzing an image. At least part of the analysis can be implemented by a data processor configured for receiving the image and executing the operations described below.

Computer programs implementing the method of the present embodiments can commonly be distributed to users on a distribution medium such as, but not limited to, a floppy disk, a CD-ROM, a flash memory device and a portable hard drive. From the distribution medium, the computer programs can be copied to a hard disk or a similar intermediate storage medium. The computer programs can be run by loading the computer instructions either from their distribution medium or their intermediate storage medium into the execution memory of the computer, configuring the computer to act in accordance with the method of this invention. All these operations are well-known to those skilled in the art of computer systems.

The method of the present embodiments can be embodied in many forms. For example, it can be embodied in on a tangible medium such as a computer for performing the method operations. It can be embodied on a computer readable medium, comprising computer readable instructions for carrying out the method operations. In can also be embodied in electronic device having digital computer capabilities arranged to run the computer program on the tangible medium or execute the instruction on a computer readable medium.

The image to be analyzed using the teachings of the present embodiments is generally in the form of imagery data arranged gridwise in a plurality of picture-elements (e.g., pixels, group of pixels, etc.).

The term "pixel" is sometimes abbreviated herein to indicate a picture-element. However, this is not intended to limit the meaning of the term "picture-element" which refers to a unit of the composition of an image.

References to an "image" herein are, inter alia, references to values at picture-elements treated collectively as an array. Thus, the term "image" as used herein also encompasses a mathematical object which does not necessarily correspond to a physical object. The original and processed images certainly do correspond to physical objects which are the scene from which the imaging data are acquired.

Each pixel in the image can be associated with a single digital intensity value, in which case the image is a grayscale image. Alternatively, each pixel is associated with three or more digital intensity values sampling the amount of light at three or more different color channels (e.g., red, green and blue) in which case the image is a color image. Also contemplated are images in which each pixel is associated with a mantissa for each color channels and a common exponent (e.g., the so-called RGBE format). Such images are known as "high dynamic range" images.

In some embodiments of the invention, the image is an image of the head or, more preferably, the craniofacial complex of a subject (e.g., an X-ray image, also referred to below as a roentgenogram or radiograph; a Computerized Tomography image, also referred to below as a CT image; or a Magnetic Resonance image, also referred to below as an MR image). These embodiments are particularly useful for medical application. For example, the analysis can include extraction of cephalometric features from the target image which can be used, in some embodiments, for assessing sleep disordered breathing (SDB) or the likelihood of SDB of the subject.

Also contemplated are thermal images, ultraviolet images, positron emission tomography (PET) images, ultrasound images, an Electrical Impedance Tomography (EIT) images, single photon emission computed tomography (SPECT) images, and the like.

As used herein, the craniofacial complex refers to an anatomical complex which comprises at least the cranium and skull-base, the dento-facial complex and soft tissue upper airways of the subject, preferably including the tongue, vellum and pharynx, and optionally also including the larynx or part thereof. Representative examples of craniofacial complexes are shown in FIGS. 1A-B, 2A-F, 5A-B, 8A-C, 9A-B, 11A-D and 12A-C.

As used herein, "X-ray image" refers to an image produced by recording changes produced in electromagnetic radiation in the X-ray range, for example, at a wavelength of from about 0.01 to about 10 nanometers.

As used herein "Computerized Tomography" refers to a technique in which a two or three-dimensional image of the internal structures of a solid object, such as a human body, is produced by recording changes produced in radiation, such as X-ray or ultrasound radiation, when transmitted through the object. A Computerized Tomography image is an image of a body structure, constructed by a computer from a series of projections (also referred to as slices), as produced by the transmitted radiation, along an axis.

As used herein "Magnetic Resonance Imaging" (MRI) refers to a technique in which an image representing the chemical and physical microscopic properties of an object is obtained by utilizing a quantum mechanical phenomenon, named Nuclear Magnetic Resonance (NMR), in which a system of spins, placed in a magnetic field resonantly absorb energy, when applied with a certain frequency. The acquisition of MR images can include a slicing technique, in which case one or more of the MR images (e.g., each MR image) is a sliced MR image which comprises a set of MR images, wherein each element in the set corresponds to a different slice of the object. The thickness of each slice can be selected to improve the signal-to-noise ratio (SNR) and/or the contrast-to-noise ratio (CNR) of the image.

Similarly to CT image and MR image, other types of images (e.g., a PET image, a SPECT image, an ultrasound image, EIT image and the like can also be sliced images.

Thus, the term "sliced image" as used herein refers to a set of images respectively corresponding to a series of projections of the imaged object along an axis.

When the method and system of the present embodiments is employed for analyzing a sliced image (e.g., a sliced CT image or a sliced MR image), the analysis can be applied either separately to each slice of the image or collectively to a three-dimensional reconstruction of the object as constructed by a data processor for a given sliced image.

The method and system of the present embodiments can optionally and preferably analyze two or more different types of images. The results of the analysis can be presented as a list, or they can be combined, for example, using a statistical procedure so as to improve the accuracy, quality and/or predictability of the analysis.

SDB consists of a continuous upper airway resistance with clinical indications ranging from snoring to Obstructive Sleep Apnea (OSA). During sleep, the pharynx cavity is narrowed and the tongue experiences a posterior displacement, resulting in a pharyngeal airflow resistance which is higher than the resistance during wakefulness. However, when the anatomy of the subject is normal, the resistance is compatible with the low tidal volume characterizing the sleep. Consequently, the breathing temporarily stops during sleep as the throat muscles relax and block the patient's airway. The patient then wakes up in order to restart his breathing, and the quality of sleep is impaired.

In OSA, the obstruction of the airways results in a disequilibrium between the forces which tend to their collapse such as the negative inspiratory transpharyngeal pressure gradient, and those which contribute to their opening such as their muscle continues tonus and the elastic properties of the velo-linguo-pharyngeal structures. The mechanisms which underlie the triggering of obstructive apnea include a reduction in the size of the upper airways, an increase in their elasticity, of their mass and a reduction in the activity of the muscle dilator. The muscle dilators are intimately linked to the respiratory muscles and these muscles respond in a similar manner to stimulation or a depression of the respiratory center. The ventilatory fluctuations observed during sleep (alternately hyper and hypo ventilation of periodic respiration) thus favors an instability of the superior airways and the occurrence of velopharyngeal obstruction. The respiratory activation of the genioglossus has been particularly noted to be ineffective during sleep.

SDB daytime symptoms include excessive daytime somnolence, chronic fatigue, and headache upon awakening and dry mouth. Prolonged SDB are related to increased risk of cardiovascular disease, stroke, high blood pressure, arrhythmias and diabetes. The cardiovascular consequences of apnea include disorders of cardiac rhythm (bradycardia, auriculoventricular block, ventricular extrasystoles) and hemodynamic (pulmonary and systemic hypertension). This results in a stimulatory metabolic and mechanical effect on the autonomic nervous system. The electroencephalographic awakening which precedes the easing of obstruction of the upper airways is responsible for the fragmentation of sleep. The syndrome is therefore associated with an increased morbidity including the consequence of diurnal hypersomnolence and cardiovascular complications.

The prevalence of sleep apnea is estimated to be 3.3% in the adult male population and increasing to almost 5% in the middle age group. Traditionally, OSA is diagnosed via polysomnography in a sleep laboratory. The evaluation involves an overnight stay in sleep laboratory, or sometimes at home using a special equipment, and monitoring of the breathing, blood tension, oxygen blood saturation level, electromyographic, electroencephalographic and other parameters during sleep. The collected data during the polysomnographic study are analyzed by a specialist. It is recognized by the present inventors that these polysomnographic studies have several significant limitations and potential drawbacks and hence it was found by the present inventors that it is advantageous to assess of the anatomic factors that predispose the airway to collapse during sleep. The present inventor found that such assessment can allow ranking of the SDB severity thereby allowing the physician to tailor the appropriate treatment modality to the individual patient. Inventors of the present invention have further found that these anatomic factors can be obtained from cephalometric analysis.

It is recognized by the present inventors that cephalometric analysis is an appropriate tool for identifying pathophysiological abnormalities in the craniofacial complex, hence also in the upper airways. Cephalometry is a simple, inexpensive and involves low radiation levels. However, several reasons have prevented cephalometric analysis from being the routine technique for evaluation of SDB. These include high complexity, lack of gold standards, and the like.

The present Inventors discovered a cephalometric analysis that can be used for assessing SDB (e.g., level of SDB) or the likelihood of SDB. In various exemplary embodiments of the invention an image of the craniofacial complex is analyzed so as to identify shapes of cephalometric structures in the image. Optionally, the identified shapes include at least one curved shape. The identified shapes are then classified according to predetermined baseline shapes, and SDB or likelihood of SDB is assesses based on the classification. A report pertaining to the assessment can then be issued. The identification and/or classification of shapes is preferably performed automatically, e.g., by a data processor or a computer supplemented by a computer software product. A preferred automated method is provided hereinbelow.

Optionally and preferably the identification and classification of the shapes is repeated for an additional image corresponding to a different viewpoint of the craniofacial complex of the same subject. In these embodiments, the assessment can be based on both classifications. In various exemplary embodiments of the invention one of the images corresponds to a lateral view of the craniofacial complex and one of the images corresponds to a frontal view of the same complex. The analysis optionally and preferably also includes measuring linear and angular measures characterizing the shapes and their sizes. These measures can also be used during the assessment.

One of the curved shapes that can be identified and classified is the shape of the tongue. It is recognized by the present inventors that one of the differences in the cephalometry between normal and SDB subjects include is the shape of soft tissue, e.g., the tongue which cannot be well expressed by the current cephalometric measurements, and the orientation of the tongue relatively to the skull-base and dentofacial complex. The tongues muscles have a role in maintaining the upper airways open during sleep breathing. The analysis of tongues anatomy can therefore aid in the assessment of the pathophysiology of SDB.

Additional shapes that can be identified and classified are the shape of the skull base and its orientation relative to the splanchnocranium, and the shape of the pharynx.

A representative example of craniofacial complex analysis is shown in FIGS. 1A-B, where FIG. 1A is a lateral view image of the craniofacial complex with several landmarks marked thereon (red dots), and FIG. 1B is the same image after identifications of the shapes of the tongue 10, and the skull base 12. In the present example, the tongue is posterior and elongated, indicating that the subject has SDB. An angle BaSN which below 127° (e.g., at least 2-3 degrees below 127°) can indicated that it is likely that the subject suffering from Acute Angulation of Skull-Base. The craniofacial complex in the case of FIG. 1 is hyperdivergent (small angle between the Ban line and the GnGo line), and the maxillais hypoplastic is underdeveloped (short PNS-ANS). The tongue is large and because of the combination of the above cephalometric parameters it is vertical and located posteriorly than the normal.

Figures 2E, 2F:
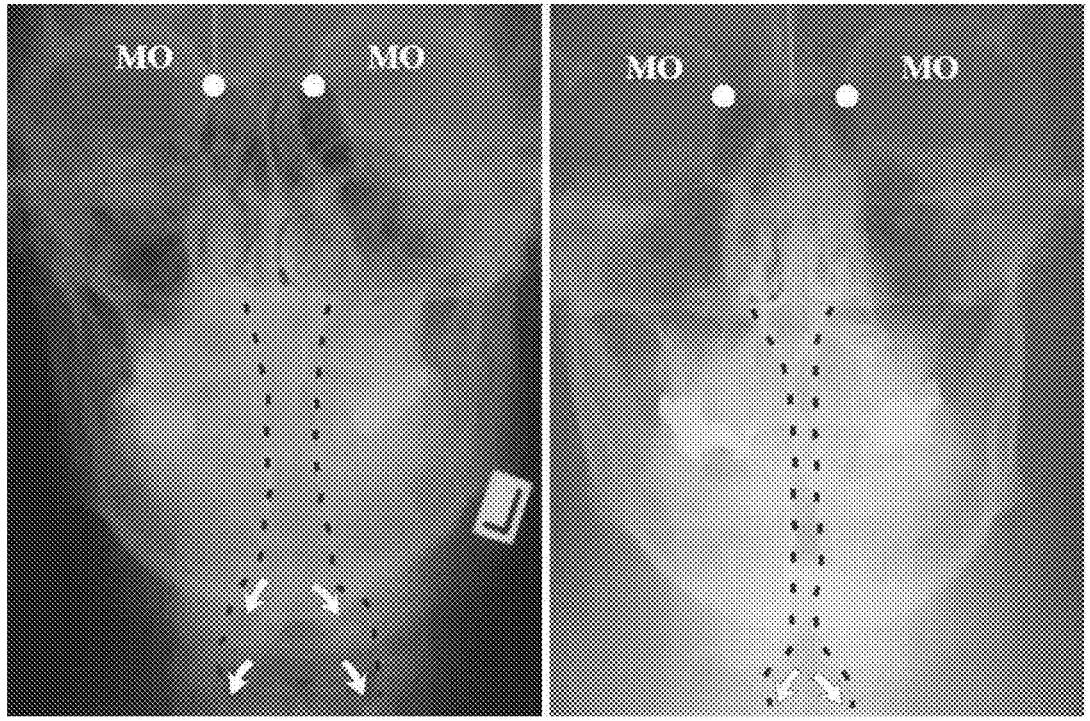
Figures 3A, 3B, 3C:
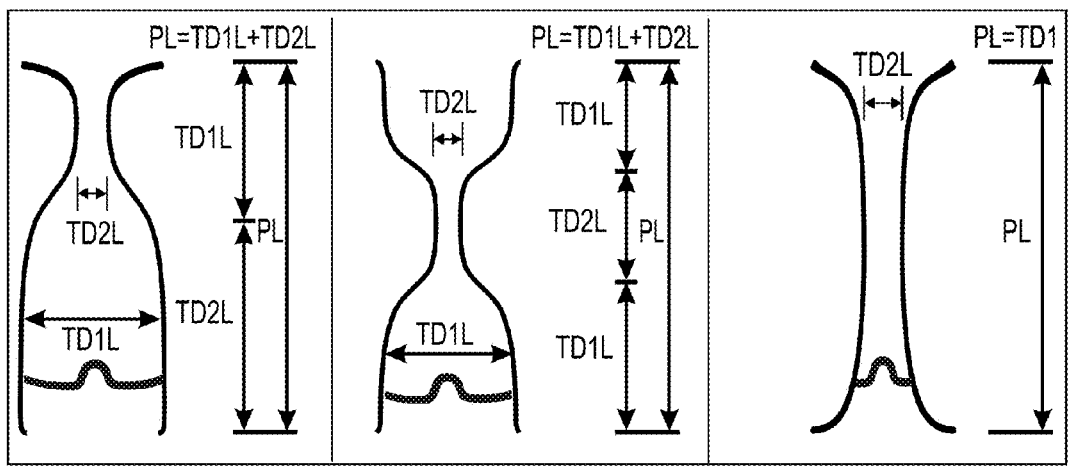

Another example of craniofacial complex analysis is shown in FIGS. 2A-F, which are frontal view images of the craniofacial complex, after identification of the shape of the pharynx 20. The shape of the pharynx can be classified into pharynx with generally parallel frontal outlines (FIG. 2A), a hourglass shape pharynx having a relatively short (e.g., about 10-20% of the total length or less) and narrowed central section and wider upper regions and lower sections (FIG. 2B), bottle shape pharynx having a narrowed upper section and a wider central and lower sections (FIGS. 2C and 2D), and a widened-tube shape pharynx having a relatively long (e.g., about 50-90% of the total length) and narrowed central section and wider upper regions and lower sections (FIGS. 2E and 2F). A set of linear measures for classifying a pharynx as a bottle shape pharynx, hourglass shape pharynx, and widened-tube shape pharynx are shown in FIGS. 3A-C, respectively.

A sufficiently wide pharynx with generally parallel frontal outlines indicates a low likelihood of SDB, while hourglass shape pharynx, bottle shape pharynx and widened-tube shape pharynx indicate higher likelihood of SDB. Additional examples of craniofacial complex analysis are provided hereinunder.

In various exemplary embodiments of the invention the analysis further comprises receiving non-cephalometric information, wherein the likelihood of SDB is assessed also responsively to the non-cephalometric information. The non-cephalometric information can include any information pertaining to the pathophysiology of the craniofacial complex that can be obtained using non-cephalometric techniques. Representative examples include, without limitation, information pertaining to nasal obstruction, glottic narrowing, adherent velum, pharyngeal collapse, epiglottic collapse and/ or edema of posterior larynx. Additional non-cephalometric information includes Body Mass Index (BMI). The non-cephalometric information can be obtained from an external source or can be measured directly.

The collection of all information, including the shapes, sizes and spatial inter-relationship (e.g., relative orientation) of the various cephalometric structures, and the non-cephalometric information can be used for calculating a Nocturnal Upper Airway Stability Index (NUASI) which is an overall index which quantifies the likelihood of SDB.

Following is a description of a method suitable for analyzing an image according to some embodiments of the present invention.

The image analysis technique described below optionally and preferably includes comparison between the image to be analyzed, and a previously analyzed image which is typically an entry of database of analyzed images. The image to be analyzed is referred to herein as a "target image," and the previously analyzed image is referred to herein as a "database image." The database image is typically associated with annotation information, and is therefore an annotated image. The annotation information can be stored separately from the imagery data (e.g., in a separate file on a computer readable medium). The annotation information can include local annotation wherein picture-elements at several locations over the image are identified as corresponding to specific features of the imaged scene. The annotation information can also include global annotation wherein the entire image is identified as corresponding to a specific scene or a specific family of scenes. For example, when the scene is the craniofacial complex, local annotation can include cephalometric landmarks that are identified over the image, and global annotation can include a specific group of individuals (e.g., a specific gender, ethnic origin, age group, etc.) and/or a specific condition (e.g., presence, absence or level of SDB) to which the craniofacial complex corresponds.

The analysis technique of the present embodiments is described below with reference to flowchart diagrams describing method operations. It is to be understood that, unless otherwise defined, the operations described hereinbelow can be executed either contemporaneously or sequentially in many combinations or orders of execution. Specifically, the ordering of the flowchart diagrams is not to be considered as limiting. For example, two or more operations, appearing in the following description or in the flowchart diagrams in a particular order, can be executed in a different order (e.g., a reverse order) or substantially contemporaneously. Additionally, several operations described below are optional and may not be executed.

Figure 4:
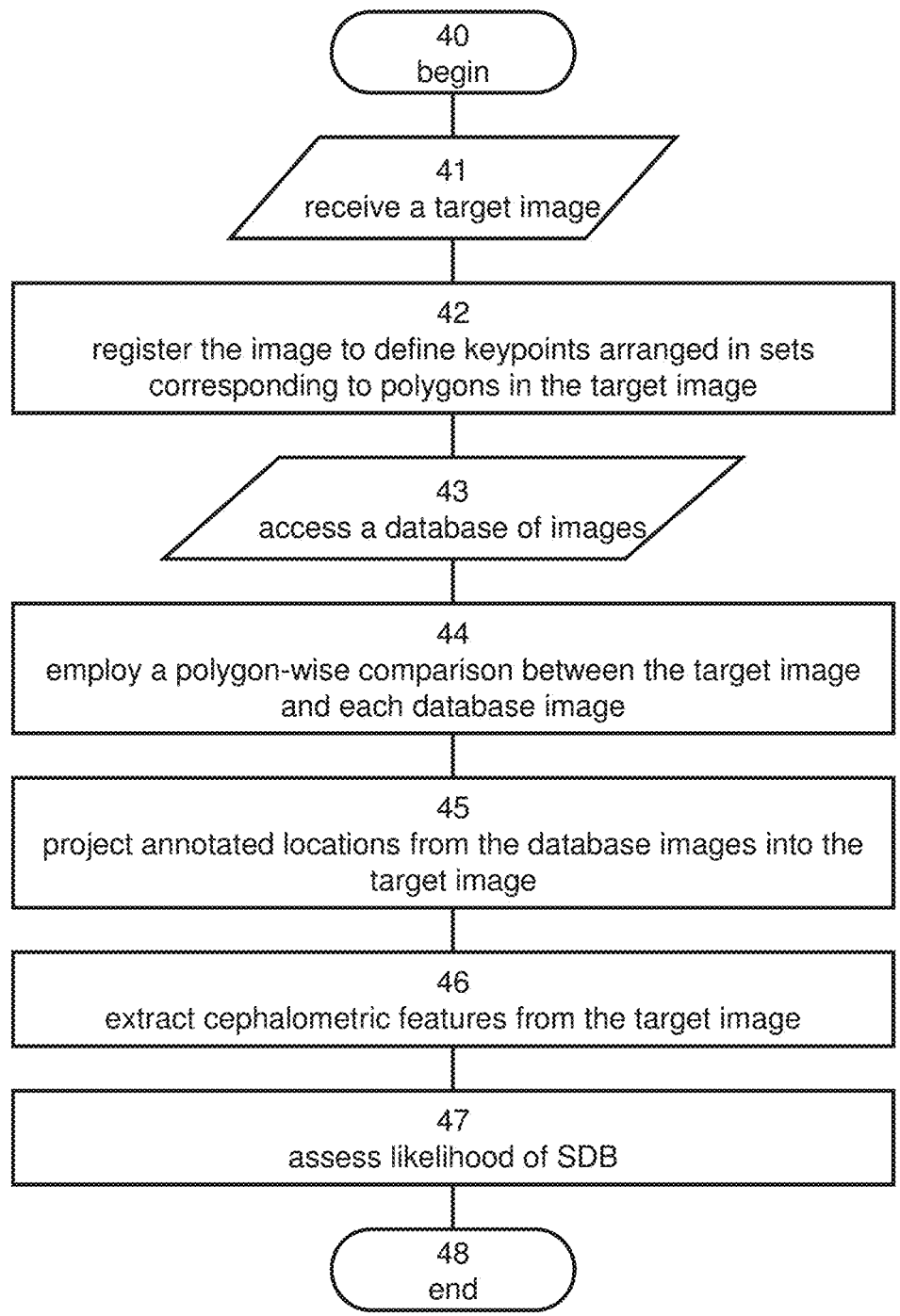

Referring now to the drawings, FIG. 4 is a flowchart diagram describing a method suitable for analyzing a target image, according to some embodiments of the present invention. The method begins at 40 and continues to 41 at which the target image is received, preferably in the form of digital image data as further detailed hereinabove. The target image can be an image of the craniofacial complex of a subject, as further detailed hereinabove.

The method proceeds to 42 at which the target image is registered to define a plurality of keypoints arranged in sets corresponding to polygons or linear segments in the target image. In various exemplary embodiments of the invention there is an equal number of keypoints in each set. For example, each set can have a triplet of keypoints, in which case each set corresponds to a triangle in the target image. Sets of other sizes, e.g., doublets, quartets, quintets, sextets, septets, octets, nonets, etc, are also contemplated.

While the embodiments below are described with a particular emphasis to polygons, which correspond to sets of at least three keypoints, it is to be understood that more detailed reference to polygon is not to be interpreted as excluding linear segments which correspond to sets of two keypoints.

The number of points that are obtained is preferably large, e.g., from a few tens to several hundred points for an image of 1600×1200 pixels. In various exemplary embodiments of the invention the keypoints are obtained together with a set of information, which is preferably in the form of a descriptor vector of a predetermined dimension, describing each such keypoint. For example, a descriptor vector can include information regarding the magnitude and direction of intensity gradients at the vicinity of each keypoint (e.g., within a distance of a few pixels from the respective keypoint). Thus, the registration of the target image according to the present embodiments results in an encoding which includes a collection of sets and associated descriptors.

A preferred registration procedure is described hereinafter and in the Examples section that follows.

The method preferably proceeds to 43 at which a database of images is accessed. The database images are both registered and annotated. The registration of the database images is preferably according to the registration protocol employed for the target image. Specifically, each database images is associated with sets of keypoints, preferably equal-size sets of keypoints, e.g., triplets of keypoints. The database images can be registered by the method or they can be stored in the database together with their registration information. The annotation information of the database images, which can be annotated cephalometric landmarks, is preferably stored together with the database.

The method proceeds to 44 at which a polygon-wise comparison is employed for comparing the target image to each of the database image.

As used herein "a polygon-wise comparison" refers to a procedure in which for a given target image and database image, each polygon in the target image is compared to each polygon in the database image, according to a predetermined set of comparison criteria. The criteria can include differences between the respective descriptors, as further detailed hereinunder.

The method continues to 45 at which the comparison is used for projecting annotated locations from the database images into the target image, thereby annotating the target image. This can be done in the following manner. For each matching between a polygon in the target image and a polygon in the database image, the method calculates an affine transformation from the database image to the target image, for the particular image regions associated with the respective polygons. If the polygon in the database image encloses or borders one or more annotated locations (e.g., cephalometric landmarks) the calculated affine transformation can be used for projecting those annotated locations into the target image. Once the target image is annotated, it can be transmitted to a computer-readable medium or a display device or a printing device, as desired.

A preferred procedure for the projection is as follows. For each pair of polygons (one from the target image and one from the database image) that are compared, a score characterizing the comparison is preferably recorded, together with the respective affine transformation and an index identifying the database image to which the polygon belongs. Once all the comparisons are completed (e.g., each polygon of each database image is compared to each polygon of the target image), the database polygons are preferably ranked according to their score, irrespectively of the image to which they belong. Thereafter, a predetermined number N of highest ranked polygons is selected. Denote these highest ranked polygons by $k_i$ (i=1, . . . , N). In experiments performed by the present inventors a value of N=50 was selected. Each polygon $k_i$, is, as stated, associated with affine transformation and an index identifying the database image to which $k_i$ belongs. In various exemplary embodiments of the invention, for each polygon $k_i$, the respective affine transformation is applied to project the annotated location enclosed by $k_i$ from the respective database image onto the target image.

It is appreciated that a given polygon in the target image can match, to some extent, more than one polygon in more than one database image. Thus, a given annotation (e.g., each cephalometric landmark) can be associated with a collection of locations over the target image. In some embodiments of the present invention a single location per annotation is obtained by employing a statistical procedure. A suitable such procedure is the mean shift algorithm described in Cheng, Y., 1995, "Mean shift, mode seeking, and clustering," IEEE Transactions on Pattern Analysis and Machine Intelligence 17:790-799.

Alternatively, the vicinity of the projected locations can be searched for a region whose appearance (e.g., shape, contrast, intensity gradients) matches the appearance of the respective landmark. This can be done, for example, by employing a classifier for the detection of predetermined appearance. A representative example for such procedure is as follows. Following the projection, a set of templates can be selected for each annotated location (e.g., anatomic each landmark), by projecting for each polygon the associated database image to the target image, and cropping a template around each point. For each location, a machine learning algorithm such as, but not limited to, support vector machine (SVM) regression can be used for training a classifier to distinguish the relevant templates from nearby templates, which can then be used for estimating the final location.

When the target image is a slice of a sliced image, the projected locations can be transferred from one slice to another. This can be done, for example, by defining the already annotated slice as a new database image and another slice of the same sliced image as a new target image, and repeating at least part of the above procedure for the new target image using the new database image.

Alternatively, the annotated locations are projected separately, and optionally also independently, onto each slice of the sliced image, using other previously annotated database images.

Still alternatively, the annotated locations are projected onto a three-dimensional reconstruction of the imaged object, as reconstructed by a data processor for a given set of slices corresponding to projections of the same object on different planes. In these embodiments, a three-dimensional coordinate system is optionally and preferably employed for describing the three-dimensional reconstruction, and used for assigning a three-dimensional coordinate is to each annotated location.

When the projected locations correspond to annotated cephalometric landmark, the method optionally and preferably proceeds to 46 at which cephalometric features are extracted from the target image based on the projected locations of the annotated cephalometric landmarks. Such features may include linear measures between landmarks, angular relations between landmarks, shapes of cephalometric structures and the like.

Figure 5A:
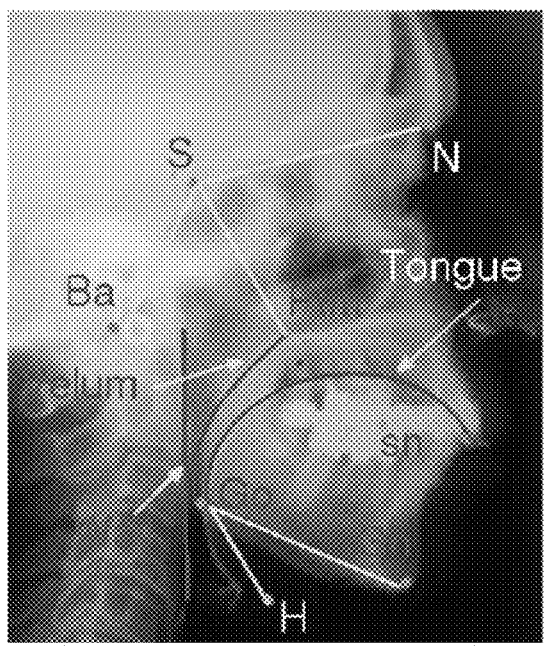
Figure 5B:
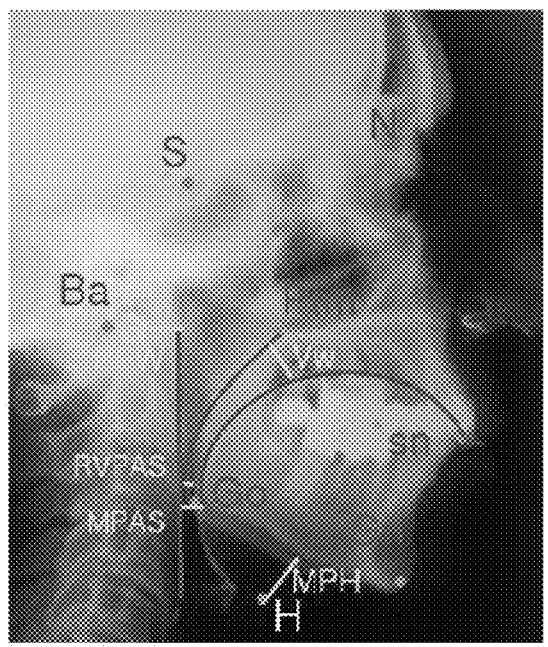

Representative examples of annotated cephalometric landmarks, measures and structures suitable for the present embodiments are illustrated in FIGS. 5A-B. The cephalometric landmarks shown in FIGS. 5A-B include gnathion (Gn), gonion (Go), basion (Ba), sella (S), nasion (N), end of tongue (sn), pterygomaxillare (Ptm) and hyoid (H). The cephalometric structures shown in FIGS. 5A-B include the tongue, the velum and the pharyngeal wall. The cephalometric linear measures shown in FIGS. 5A-B include the maximal width of the velum (Vw), the minimum distance between the velum and the posterior pharyngeal wall (RVPAS), the distance between the hyoid (H) and the line connecting Gn and Go (MPH), the distance from the Ba to the wall (PPW), and the minimum distance between the tongue and the posterior pharyngeal wall (MPAS). The cephalometric angular measures shown in FIGS. 5A-B include the bony nasopharyngeal angle (BaSPtm), the skull base angle (BaSN) and the mandibular plane hyoid angle (GnGoH). Also contemplated, is a skull base orientation angle which can be defined, for example, with respect to an imaginary horizontal line (not shown). Further contemplated are various other angles characterizing the skull, e.g., the angle SBaPtm, and the like.

It is to be understood that it is not intended to limit the scope of the present invention to the above measures, and that many additional measures can be employed. For example, in some embodiments of the present invention, measures that characterize the shape, orientation and spatial relative location and relationship with other craniofacial components of the velum, other than the aforementioned maximal width, are employed.

It is expected that during the life of a patent maturing from this application many relevant cephalometric landmarks, structures and measures will be developed and the scope of the terms cephalometric features are intended to include all such new technologies a priori.

In some embodiments of the invention cephalometric feature extraction includes modeling a shape of one or more of the cephalometric structure, and fitting the model to annotated landmarks in the target image. For example, the outline of the tongue or part thereof can be modeled as an ellipse of a section of an ellipse, the velum can be modeled using a basis spline (e.g., a four knot spline), and the pharyngeal wall can be modeled as a straight line.

Once the cephalometric features are extracted, the method optionally proceeds to 47 at which the SDB (e.g., level of SDB) or likelihood of SDB is assessed based, at least in part, on the extracted cephalometric features. Non-cephalometric can also be received and combined with the cephalometric information for better assessment, as further detailed hereinabove.

Optionally and preferably, the analysis is repeated for an additional target image of an additional view point of the craniofacial complex of the same subject. For example, one target image can correspond to a lateral view of the craniofacial complex and another target image can correspond to a frontal view of the same complex. The two different viewpoints can be used to obtain three-dimensional information regarding the cephalometric structures. For example, the information from the two images can be combined for constructing a three-dimensional model of the shape of the structures. Alternatively or additionally, each image can be analyzed separately wherein the assessment is based on the individual analyses without constructing a three-dimensional model of the structures.

In some embodiments of the invention the method calculates one or more indices based, at least in part, on the extracted cephalometric features. For example, in some embodiments a respiratory disturbance index (RDI) of the subject is calculated. This can be done, for example, using a linear Support Vector Regression model. With a linear regression model, the RDI can be computed as a linear function of the input parameters. Alternatively, one can use radial basis functions (RBF) or other models.

In some embodiments, the characteristic pharyngeal airflow resistance is calculated, for example, according to the following procedure.

On frontal cephalometry, the pharynx is visualized from the floor of the nose downward to the pyriform sinuses. Additional velopharyngeal soft tissue measures can be the pharyngeal width in its narrow segment (TD1), the pharyngeal width in its wide segment (TD2), the lengths of those segments (TD1L and TD2L, respectively), and the pharyngeal length which is defined as PL=TD1L+TD2L and which is equivalent to the length of pharynx measured from the floor of the nose to the pyriform sinuses. Another cephalometric parameter can be the medial orbital-medial orbital distance (MOMO). Based on these measurements, the ratio of transverse pharyngeal diameter (TD1R) and the ratio of transverse pharyngeal diameter (TD2R) can be calculated. These ratios can be used to identify the soft tissue transverse narrowing of the velopharynx relative to the midfacial skull base bony limits. The TD1R and TD2R parameters are convenient measures since they refer to the dimension of the pharynx as proportional components of the cranioviscerofacial complex.

PL, the cross-sectional area (A), and a, a constant characteristic of the material making up the pharyngeal tissue, affect the resistance of the velopharynx as a tube. The pharyngeal resistance is proportional to PL, and inversely proportional to A:

$$PR = \alpha \frac{PL}{A}$$

When the velopharynx is composed of 2 segments of different diameters PR can be calculated as follows:

$$PR = \alpha \left[ \frac{TD1L}{RVPAS \times TD1} + \frac{TD2L}{MPAS \times TD2} \right],$$

where RVPAS and MPAS are linear measures defined above. RVPAS and MPAS are measured by cephalometric analysis of lateral view of the craniofacial complex, wherein TD1, TD2, TD1L and TD2L are measured by cephalometric analysis of frontal view of the craniofacial complex.

When the velopharyngeal diameter is uniform, e.g., in the tube-shaped velopharynx, PR can be calculated as follows:

$$PR = \alpha \frac{TD}{\frac{1}{2}(RVPAS + MPAS) \times TD1},$$

The identification and classification of the shapes can also be repeated one or more time for an additional image corresponding to the same viewpoint of the craniofacial complex of the same subject. These embodiments are particularly useful for assessing changes in the craniofacial complex over time. For example, one image can be captured before treatment and another image can be captured during or after treatment, and the method can estimate the efficiency of the treatment base on changes identified in cephalometric features or lack thereof. The treatment can also include implantation or mounting of a dental device, and the method can estimate the effect of the dental device on the craniofacial complex based on changes identified in cephalometric features or lack thereof.

Also contemplated are embodiments in which a series of images corresponding to the same viewpoint of the craniofacial complex of the same subject at different times (e.g., at intervals of one or more weeks, of one or more months, or one or more years) are analyzed for the identification and classification of the shapes. Such series of analysis can be used for assessing a progress or lack of progress in a disease or condition pertaining to the craniofacial complex. The method can optionally and preferably provide a prognosis estimate based on the identified progress or lack thereof.

The method ends at 48.

Figure 6:
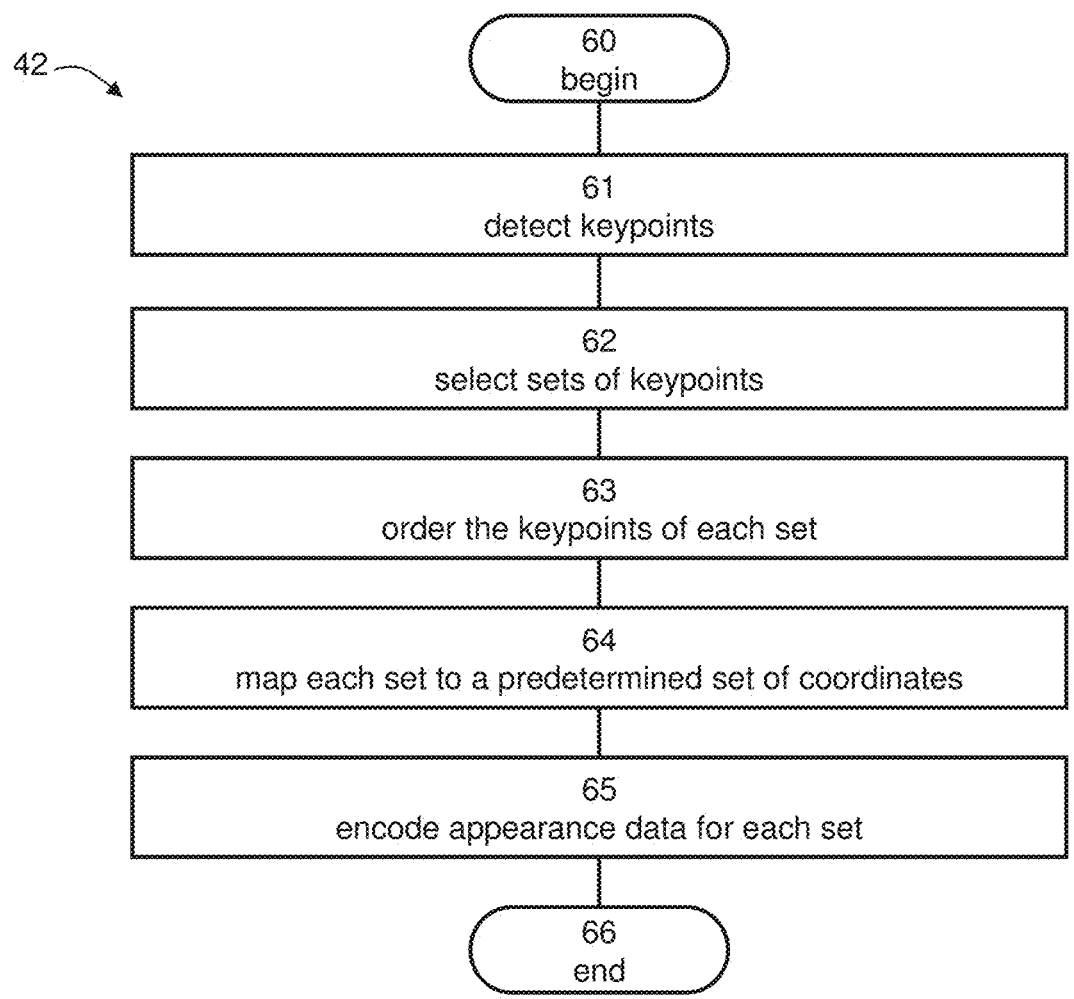

FIG. 6 is a flowchart diagram describing an image registration method, according to some embodiments of the present invention. The registration method can be used for executing registration 42 of FIG. 4.

The method begins at 60 and continues to 61 at which a collection of keypoints is detected. The keypoints are typically distinctive points on the image, such as points on corners and edges, and they can be obtained using any procedure known in the art for detecting keypoints (sometimes referred to in the literature as "attention points" or "interest points") in an image. Representative examples include, without limitation, Difference of Gaussians (DoG) operator, Laplacian-of-Gaussian (LoG) operator, a Harris operator, Harris-Laplace operator, and the like. In some embodiments of the present invention the DoG is employed (to this end see, e.g., U.S. Published Application Nos. 20090238460, 20050286767, and 20070003165).

In various exemplary embodiments of the invention the keypoints are obtained together with a set of information, which is preferably in the form of a descriptor vector of a predetermined dimensionality, describing each such keypoint. The associated descriptor vectors can be obtained using any known technique for generating descriptor vectors. Representative examples include, without limitation, Scale Invariant Feature Transform (SIFT) descriptor or any variant thereof, such as Gradient Mirroring and/or Edge Precursors variants (to this end see, e.g., U.S. Pat. No. 6,711,293).

The method continues to 62 at which sets of keypoints are selected from the collection of keypoints. Optionally, as stated, there is an equal number of keypoints in each set (e.g., triplets, quartets, quintets, etc.). The sets are preferably selected in a random manner from the collection of keypoints. Optionally and preferably, one or more constraints are imposed on the selection. The constraints typically relate to the size and shape of the corresponding polygon. For example, sets corresponding to polygons having an area or aspect ratio which is outside a predetermined range can be excluded. In experiments performed by the present inventors, a set was excluded if it corresponded to a triangle whose area was less than 20 square pixels and whose smallest angle was less than 15°.

The method optionally and preferably continues to 63 at which the keypoints in each set are ordered so as to reduce the overall number of sets. For example, when the sets are triplets of keypoints, the ordering provide a 3!=6 fold reduction in the number of triplets. The ordering can be according to any ordering criterion or set of criteria. The present inventors found that it is useful to order the keypoints in each set according to the descriptor vectors associated with the keypoints in the set. This can be done by applying to the database of images a procedure for detecting keypoints together with associated information to provide a large group of features, projecting the descriptor vectors found at 61 onto the first principal component of this group, and using this projection as an ordering operator. Consider, for example, a database of images which is analyzed by DoG SIFT to provide a multiplicity of SIFT descriptor vectors. This multiplicity can be arranged as a large matrix whose columns are the SIFT descriptor vectors of the database. A principal component analysis can be applied to obtain the eigenvector with the largest eigenvalue of the matrix. The descriptor vectors of the target image can then be projected onto this eigenvector to provide an ordering operator.

The method optionally and preferably continues to 64 at which each set is mapped to a predetermined set of coordinates. Preferably, the same set of coordinates is used for all sets. Thus, in these embodiments, the vertices of each polygon are mapped to predetermined and fixed coordinates. For example, the predetermined set of coordinates can correspond to a regular or nearly regular polygon (e.g., an equilateral triangle or the like in case of triplets, a square or the like in case of quartets, a regular pentagon or the like in case of quintets, etc.). At 65 the method encodes appearance data for each of the polygons. This can be done by defining a region enclosing the polygon and recording the histogram of edge directions at the enclosing region, e.g., using SIFT descriptor representation or any other suitable representation, such as, but not limited to, PCA-SIFT [Ke et al., "PCA-SIFT: A More Distinctive Representation for Local Image Descriptors," 2004, Computer Vision and Pattern Recognition], Histograms of Oriented Gradients (HoG) [Dalai et al., 2005, "Histograms of Oriented Gradients for Human Detection," CVPR '05: Proceedings of the 2005 IEEE Computer Society Conference on Computer Vision and Pattern Recognition, 886-893], GLOH [Krystian et al., 2005, "A performance evaluation of local descriptors," IEEE Transactions on Pattern Analysis and Machine Intelligence, 10, 27, pp 1615-1630]. The present inventors found that it is useful to employ triplets, to map them by an affine transformation into a nearly equilateral triangle, whose vertices are at coordinates (1,1), (128, 1) and (64,128), and to define the enclosing region as a square whose vertices are at coordinates (1,1), (128,1), (128,128) and (1,128). Nevertheless, it is not intended to limit the scope of the present invention to this particular selection of coordinates, and one of ordinary skills in the art, provided with the details described herein would know how to select other set sizes and/or coordinates.

The method ends at 66.

FIGS. 7A-B are schematic illustration of a system 70 for analyzing an image, according to some embodiments of the present invention. System 70 can be used for executing the method described above with reference to FIGS. 4 and 6. System 70 can be implemented in a data processor 72 having a plurality of modules (see FIG. 7A). Alternatively, data processor 72 can be a general purpose computer supplemented with a computer software product 74 (FIG. 7B), comprising a computer-readable medium in which program instructions are stored, which instructions, when read by the computer, cause the computer to receive an image via an input unit 82 and execute the method as described above.

Referring to FIG. 7A, system 72 can comprise an input unit 82 through which the target image is received, an image registration module 76 for registering the target image as further detailed hereinabove, a comparison module 78 configured for accessing a database of registered and annotated images, and employing a polygon-wise comparison between the target image and each database image, and a projector module 80 configured for projecting annotated locations from the database images into the target image, as further detailed hereinabove. In some embodiments of the present invention, system 70 comprises an image aligning module 90 configured for aligning the target image and the database image according to the annotated locations.

In some embodiments of the invention system 70 comprises a cephalometric feature extraction module 84 configured for extracting cephalometric features from the target image based on the annotated locations, as further detailed hereinabove. System 70 can optionally comprise an SDB assessment module 86 configured for assessing SDB or the likelihood of SDB, as further detailed hereinabove. Optionally and preferably system 70 comprises various calculators, collectively shown at 88. Calculators 88 can be configured to calculate any of the above measures, including, without limitation, cephalometric measures, RDI, pharyngeal airflow resistance and the like.

As used herein the term "about" refers to ±10%.

The word "exemplary" is used herein to mean "serving as an example, instance or illustration." Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments." Any particular embodiment of the invention may include a plurality of "optional" features unless such features conflict.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Example 1

Exemplary Cephalometric Features

The following example describes several cephalometric features that can be used, preferably in one or more combinations, for assessing the likelihood of SDB, according to some embodiments of the present invention.

Figure 8A:
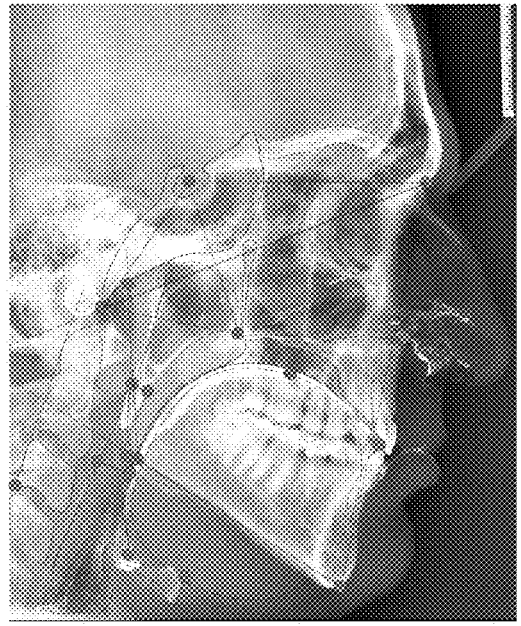
Figure 8B:
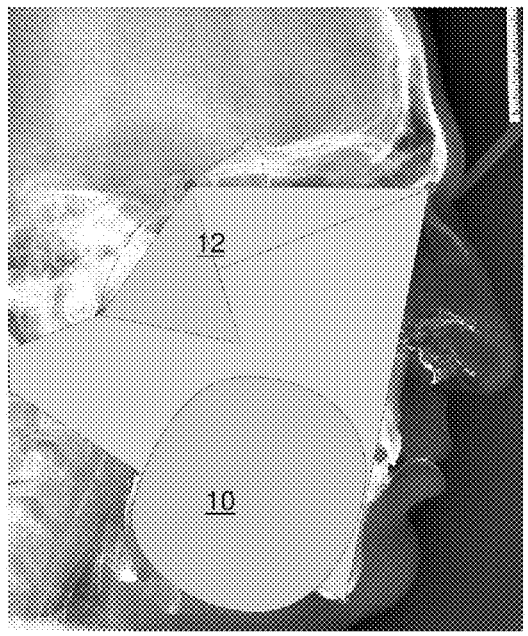
Figure 8C:
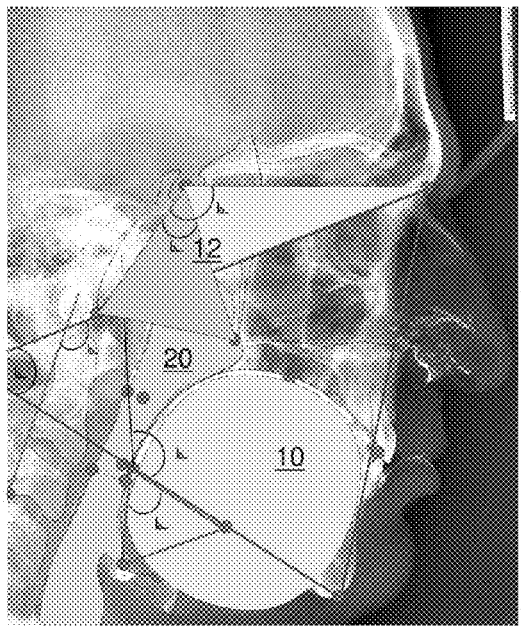

FIG. 8A is a target X-ray image showing a lateral view of the craniofacial complex of a subject, following projection of cephalometric landmarks onto the image. For clarity of presentation, the annotations of the landmarks are not shown. FIGS. 8B and 8C show the same image following cephalometric feature extraction according to some embodiments of the present invention. As shown, the extraction provides the shape of the tongue 10 and its position, the skull base 12 (shown as two adjacent triangles) and the pharynx 20. Note the differences between the craniofacial complex of this image and the craniofacial complex shown in FIG. 1B. For example, in FIGS. 8B and 8C, the tongue is more anterior and the cluster of the cephalometric parameters indicate that the patient is likely suffering from severe SDB. Nevertheless, the likelihood that the respective subjects suffer from SDB is high both for FIG. 1B and FIGS. 8B-C.

Figure 9A:
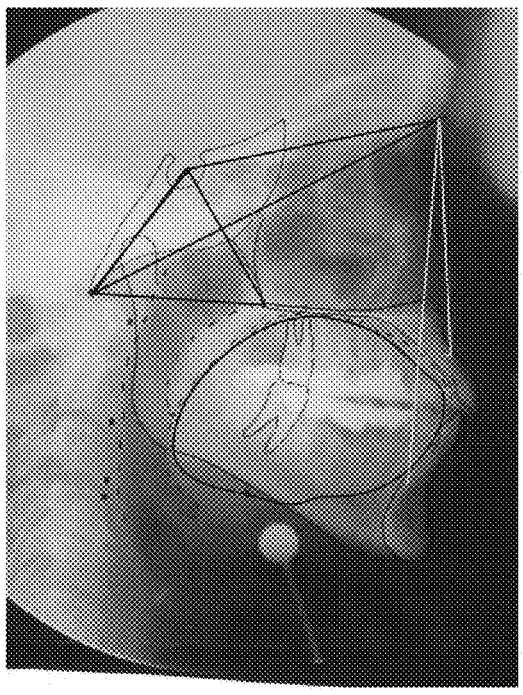
Figure 9B:
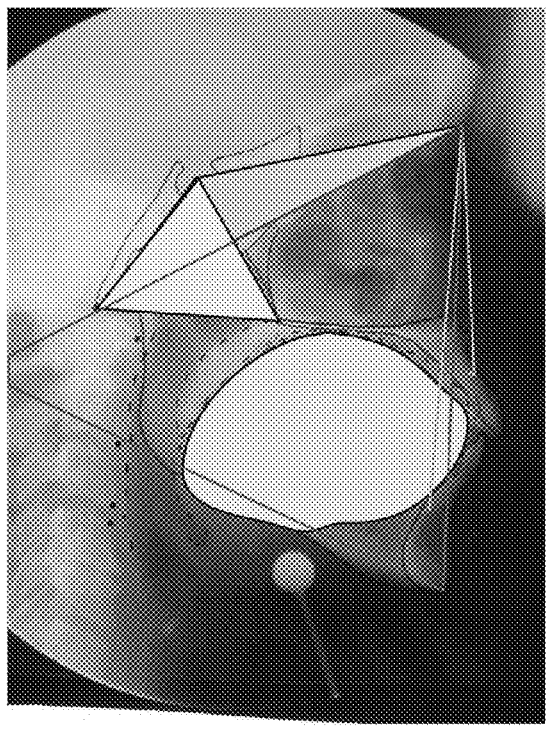

FIGS. 9A and 9B show another example of cephalometric feature extraction. This subject can be assessed as having normal breathing during sleep, or very low likelihood of SDB. The tongue is not big, its structure extends horizontally more than vertically, and its location is anterior relative to the skull base.

Figure 10A:
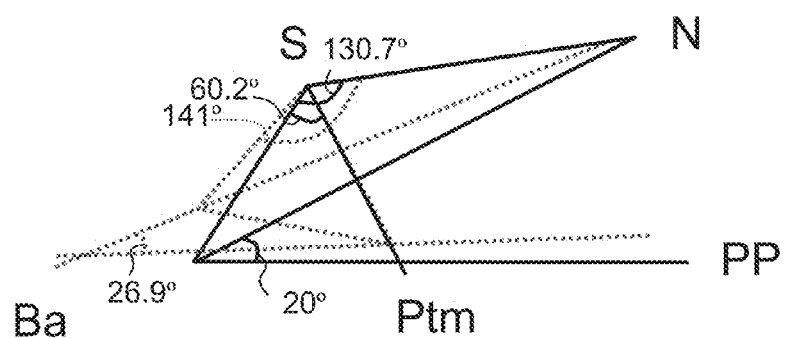
Figure 10B:
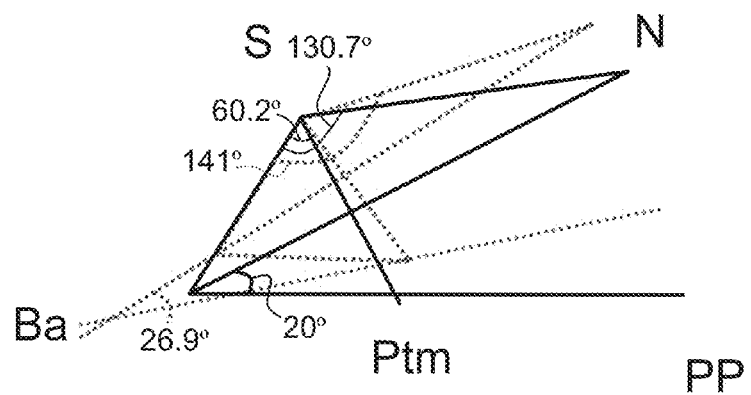
Figure 10C:
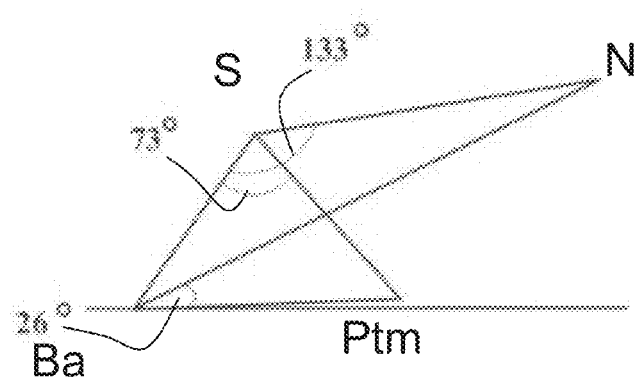
Figure 10D:
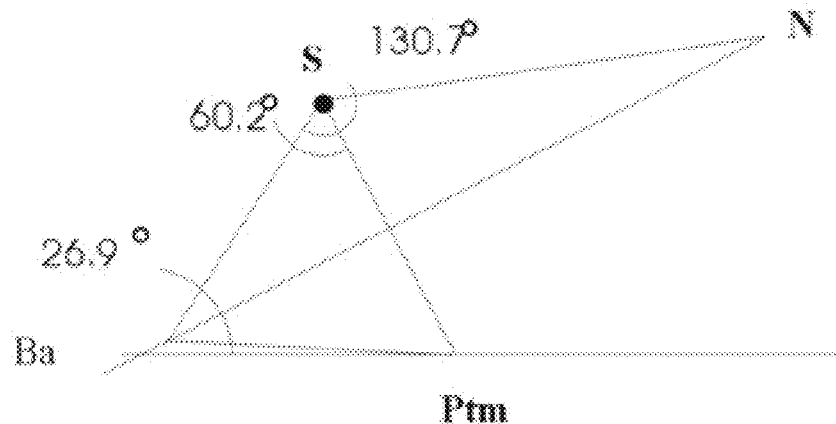
Figure 10E:
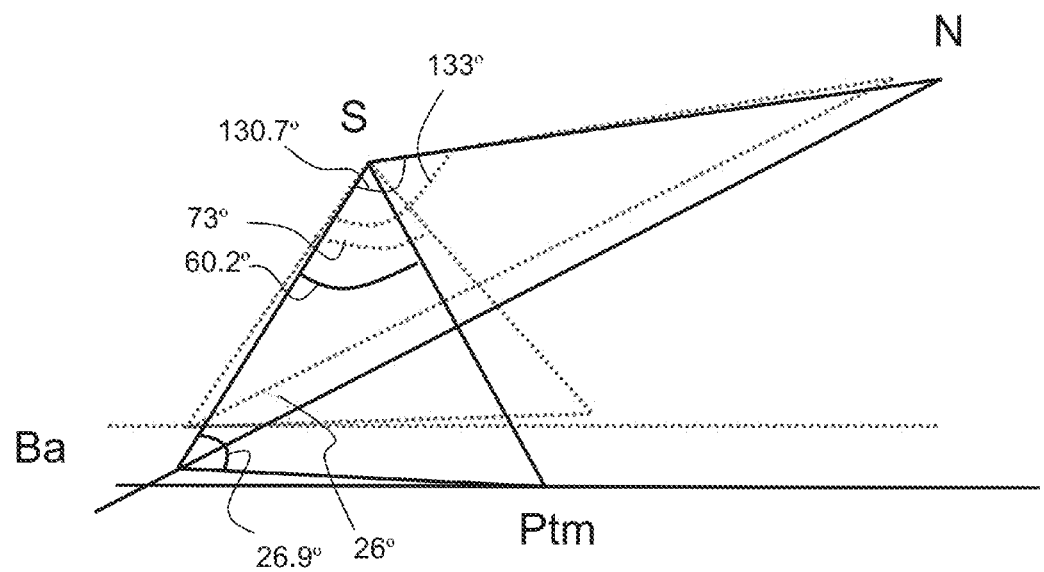
Figure 10F:
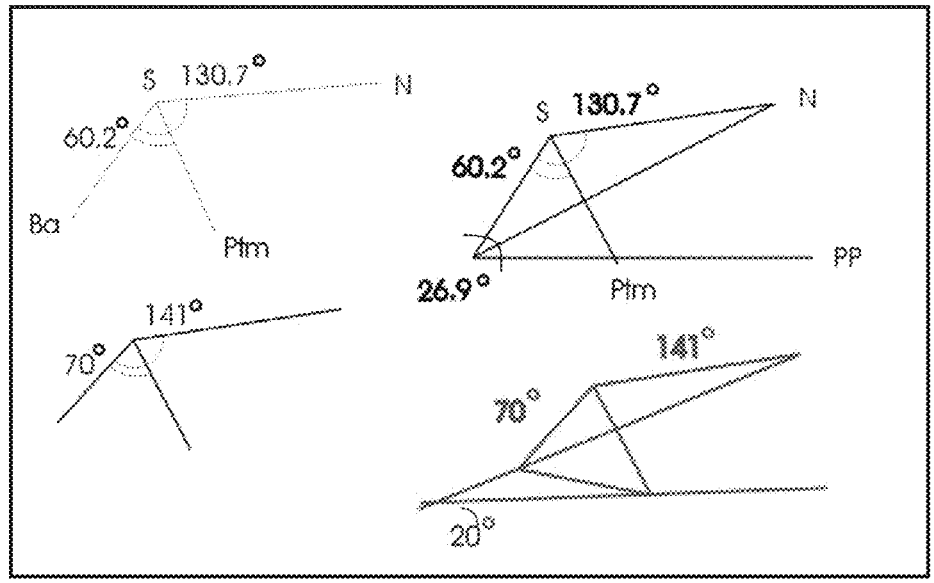
Figure 10G:
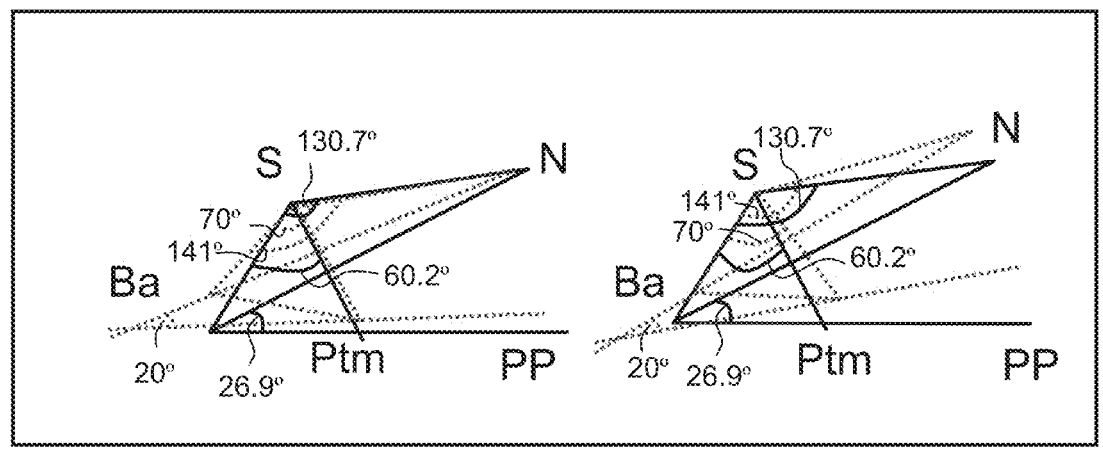
Figure 10H:
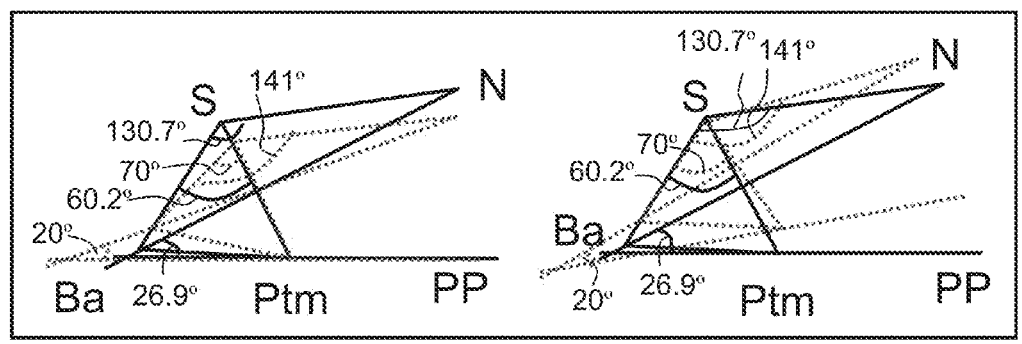

FIGS. 10A-H show various examples of angular measures between cephalometric features associated with the base of the skull. The images show measurements of angles, between the Ba-S line and the Ba-Ptm line (skull base orientation angle), between the Ba-S line and the S-Ptm line, and the Ba-S line and the S-N line (skull base angle). Also contemplated, but not shown for clarity of presentation, is an angle between the Ba-S line and the S-N line. FIG. 10D shows average numbers for a normal control group. The black lines and angle values in all other figures correspond to this group, while the red lines and angle values correspond to the tested subject. The images demonstrate that when the skull base has different angles, its projection has a different appearance. The images also demonstrate that when two individuals have the same or similar skull bases angles, the skull base orientation may be different.

Generally, the likelihood SDB is higher for skull base angles which are more acute. The likelihood of SDB is also higher for a skull base which is shorter. Additionally the likelihood of SDB is higher when the posterior part of the skull base (defined between the landmarks Ba, Ptm and S) has an angle which is too acute. For example, a bony nasopharyngeal angle which is below 55° can indicate high likelihood for SDB, even for an overall skull base angle (between the Ba-S and the S-N lines) which is within the norm. Another indication for elevated likelihood for SDB is the distance between the landmarks S and Ptm is shorter relative to the norm. The likelihood for SDB also increases with for forwardly inclined skull bases relative to the normal orientation.

Example 2

Automated Extraction of Cephalometric Features

This example describes an automated process for extracting cephalometric features. The cephalometric landmarks are detected automatically using a registration method, and anatomical structures are detected automatically thereafter. This example also demonstrates prediction of RDI based on the automatic measurements.

Image Registration

Each image is represented by a set of local regions, each associated with its own affine coordinate frame. Such a representation is sometimes called a Local Affine Frames (LAF) representation. In the literature LAFs are derived based on Maximally Stable Extremal Regions (MSERs) [Matas et al., "Robust wide baseline stereo from maximally stable extremal regions," The British Machine Vision Conf. (2002) 384-393]. In this example, triplets of keypoints were used as the basis for the LAFs, each detected using the DoG interest point operator [Lowe, D. G., 2004, "Distinctive image features from scale-invariant keypoints," International Journal of Computer Vision 60(2):91-110].

The SIFT DoG operator was applied to the image obtaining a large group of keypoints $p_1, \ldots, p_n$ (n varied from 300 to 600).

A large number of triplets, $n_T$, was randomly selected (in all the experiments of this example $n_T=10,000$).

The points of each triplet were ordered to provide a 6 fold reduction in the number of potential triplets. The order was obtained by computing for each keypoint the local SIFT descriptor, and then projecting the descriptor vector to the first principle component obtained from a large group of SIFT features that were collected beforehand. Each triplet $T_i=\{p_{i,1}, p_{i,2}, p_{i,3}\}$, $i=1, 2, \ldots, n_T$ was ordered such that $p_{i,1} < p_{i,2} < p_{i,3}$, where the order was given by the projection of the SIFT vector.

An affine transformation that maps the three points of each triangle to the coordinates (1,1), (128,1), (64,128) was computed. The transformation was used to warp the image. Thereafter, an enclosing square of corner coordinates (1,1) and (128,128) was used to obtain local appearance information for each triplet. For each triangle the histogram of edge directions at the enclosing square was recorded using the SIFT descriptor. The enclosing square was required since the SIFT implementation that was used, calculated the descriptors on rectangular regions and not triangles.

Comparison to Database Images

After each image (I) was encoded as a collection of triplets and associated descriptors, it was compared to another image (J). The matching score between pairs of triplets, one from I and one from J, was provided by the distance measure of the SIFT descriptors. The highest scoring pairs provided information on the overall match quality. FIGS. 11A-D compare the triplet-based matches of the present embodiments (FIGS. 11A and 11C) to matches based on DoG keypoints (FIGS. 11B and 11D). FIGS. 11A and 11B show frontal view of the craniofacial complex and FIGS. 11A and 11B show layeral view of the craniofacial complex.

Broadly speaking, coherent matches produce generally parallel lines. As shown in FIGS. 11A-D the triplet-based technique of the present embodiments provides matches that are much more coherent than the conventional DoG based technique. The top row demonstrates results on frontal cephalometric images.

Feature Extraction

Training images were manually marked with the relevant anatomical landmarks by cephalometric experts. Two different sets of tracings and measurements were prepared, and the mean values of the two sets of measurements were used. A group m of 8 cephalometric landmarks was employed: m={Gn, Go, Ba, S, N, sn, Ptm, H}, as further explained hereinabove. For a given an unannotated target image $I_t$, the registration technique described above was employed in order to find a multitude of matching LAFs between $I_t$ and each of the database images $I_j$, $j=\{1, 2, \ldots, m_t\}$, where $m_t$ is the number of images in the database.

Each LAF matching provided: (i) a score computed from the distance of the SIFT descriptors; (ii) a training image index, and (iii) an affine transformation between that training image and the test image. The 50 LAFs with the highest scores were selected from the pool of all LAFs. Then, the associated affine transformations were used to transform the locations of the landmarks from the training images to the test image. This process results in a collection of 50 projected locations per anatomical point in the test image. A single location per landmark was obtained by employing a mean shift algorithm [Cheng et al., "Mean shift, mode seeking, and clustering," IEEE Transactions on Pattern Analysis and Machine Intelligence 17 (1995) 790-799] to locate the mode of each group of landmark projections.

FIG. 12A shows the projected locations on the target image. The chosen points per each anatomical landmark are marked by the same color and the green dots mark the correct location. As shown, at least one location per landmark is accurate.

Following the projection, a fine-tuning procedure was applied in order to find the exact location of each landmark. A set of templates was selected for each anatomical landmark, by projecting for each LAF the associated database image to the target image, and cropping a template around each anatomical point. For each landmark, an SVM classifier was trained to distinguish the relevant templates from nearby templates. The resulting detector was applied in the vicinity of the initial mean-shift based estimation, and the maximum detector score was used to select the final location. Alternatively, other techniques, such as seeking nearest edge points, can be employed.

Once the landmarks were localized, three angular measurements were extracted: the skull base angle (BaSN), the bony nasopharyngeal angle (BaSPtm), and the mandibular plane hyoid angle (GnGoH).

Detection of Cephalometric Structures

The tongue, velum and posterior pharyngeal wall were modeled. Each cephalometric structure was fitted to a suitable geometric shape, whose parameters were searched in a range dictated by the database images.

In order to reduce the variability in the parameters of the structures, the images were first aligned with accordance to the locations of the eight anatomical feature points. For each landmark, the mean location in all database images $\bar{m}=\Sigma_{i=1}^{m_i} m_i$ was obtained. For a given image $I_j$ (database or target), the affine transformation that minimizes the least-squares error from $m_j$ to the mean $\bar{m}$ was computed and applied to and its landmarks. All anatomical structures were detected using the aligned images. Nevertheless, the actual measurements were performed after aligning the detections back to the original coordinate system.

FIG. 12B shows the tongue fitting procedure. The relevant part of the tongue is from its intersection with the contour of the chin towards the mouth's end (sn). An ellipse $E=ax^2+bxy+cy^2+dx+ey+f=0$ was found to provide a good fitting. Since an ellipse is defined by five degrees of freedom, and since the two landmarks Go and sn are known to be on the tongue, three more degrees of freedom are to be evaluated. To this end a search in a parameter space that was defined by the anatomical points was performed. Three lines were defined: a first line from Gn to Ba, a second line from Gn to Ptm and a third line forming an angle twice as large as the angle BaGnPtm. The ellipse was defined by the points Go and sn and the intersection of its top part with the three lines. The distances of these three intersection points from Gn were used as the ellipse parameters. The suitable range for each parameter was estimated from the database images. This set of three parameters was more compact than the range of the generic ellipse parameters, since the tongue may be tilted at various angles depending on the anatomy of each subject. The actual fitting was performed by an exhaustive search in these ranges, and the quality of each hypothesis ellipse was measured by the edge intensity along its path.

FIG. 12C shows the fitting procedure of the velum and pharyngeal wall. In order to measure the velar width (VW), the velum was detected in the region to the left of landmark Ptm and the maximum distance to the tongue was measured. The velum was modeled using a cubic B-spline with four knots [Press et al., "Numerical Recipes 3rd Edition: The Art of Scientific Computing," Cambridge University Press (2007)]. The coordinates of the first and last knots were fixed at Ptm and Go respectively. Using similar ideas to the tongue fitting, two lines that intersect the velum were drawn from the Gnathion (Gn). The valid range was measured from the tongue to the velum in the database images, and were used as the searching area for the two additional knots. The B-splines were iteratively fitted until a best fit was obtained.

The pharyngeal wall was modeled by a straight line. The model was parameterized by the intersection of the pharyngeal wall line with the two lines GnBa and GnGo, and the search was performed as above in a range dictated by the database images. The red lines in FIG. 12C indicate the detected structures and the yellow lines are the 4 line measurements employed for fitting.

Results 70 cephalometric images of patients with varying degrees of OSA were obtained. All images were taken in accordance with recognized standards: the head was oriented in the Frankfurt horizontal plane and stabilized with a head-holder; the teeth were in habitual occlusion with lips together, and the tongue relaxed in the floor of mouth. Exposures were taken during mid-expiration following a moderately deep breath. Therefore, the variation in pose is minimal.

The dataset was randomly split into 25 target images and 45 database images. The experiments were repeat the experiments 10 times. The results discussed below are mean results that were computed automatically on the target images.

Table 1 below compares the accuracy of the landmarks discussed in Finkelstein et al., supra with the manual detection and three other approaches (a=Rueda et al., b=Yue et al., and c=Hutton et al., supra).

TABLE 1

| <5 mm(%) | <4 mm(%) | <3 mm(%) | <2 mm(%) | mean (mm) | Landmark |
|---|---|---|---|---|---|
| 100 (98°) | 100 (78[b]) | 100 (70°) | 100 (39[a], 76[6]) | 0.48 (2.29[a], 5.5[c]) | S |
| 100 (92°) | 100 (92[b]) | 100 (69°) | 100 (37°, 83[b]) | 0.53 (2.67[a], 5.0[c]) | Ptm |
| 96 | 96 (89[b]) | 96 | 91 (86[b]) | 1.32 (5.6[c]) | N |
| 91 (99°) | 87 (100[b]) | 83 (86°) | 83 (73°, 98[b]) | 1.21 (1.58[a], 2.7[c]) | Gn |
| 95 (67°) | 83 (94[b]) | 74 (44°) | 52 (26°, 86[b]) | 2.32 (3.88[a], 5.8[c]) | Go |
| 87 (92°) | 78 (76[b]) | 74 (68°) | 65 (38°, 69[b]) | 2.06 (2.7°) | Ba |
| 39 | 30 | 22 | 13 | 6.4 | H |

Accurate results were obtained for landmarks S, Ptm, Gn and N, even though S and Ptm are not located on clear edges. Comparing to Rueda et al. and Hutton et al., the method of the present embodiments achieved better mean error for all reported landmarks. Comparing with Yue et al., the method of the present embodiments provides better results for S and Ptm and similar results for N, Ba and Gn. Regarding landmark Go, Yue et al. assumed that the landmark can be found by tracing the edge that starts from Gn (referred to as "Me" in Yue et al.), however, this assumption does not hold in many of the images analyzed in the present example where the two sides of the mandible are visible (see the double line in FIGS. 5A-B). In such cases, the location of Go is not situated on this edge point. Results for H are not reported in previous work.

The automatic line measurements were also compared with manual measurements. The mean absolute errors and standard derivations (x±y) achieved were: Vw 0.94±0.78, RVPAS 1.3±1.3, PPW 2.3±2.2 and MPH 3.8±3.4. The errors in computing Vw and RVPAS are very low. The error in detecting MPH was due to the difficulty of finding landmark H. However, considering the inter-observer variance between clinicians in marking this landmark, the automatic results of the present embodiments are in the acceptable range.

The RDI (hence also the severity of the SDB) was also predicted. In the analyzed target images, the RDI varied from 5 (borderline healthy) to 77 (severe OSA). The prediction was performed via a linear Support Vector Regression model, that was based on either: (1) The three angles measured; (2) The 4 line measurements; (3) a concatenation of (1) and (2); and as a baseline, (4) The Body Mass Index (BMI). Table 2 below summarizes the RDI prediction results. In Table 2, column 2 lists the mean squared RDI error, columns 3 and 4 list the percentage of cases that have a relatively low RDI error (<7.5) and those with a more moderate error (<15), respectively. It is noted that night-to-night variability in RDI computations at sleep clinics displays a standard deviation of 7.2 [Mosko et al., 1988, "Night-to-night variability in sleep apnea and sleep-related periodic leg movements in the elderly," Sleep 11(4): 340-348].

TABLE 2

| error < 15(%) | error < 7.5(%) | Mean Squared Error (MSE) | Method |
|---|---|---|---|
| 61 | 26 | 324 | Angles |
| 53 | 30 | 393 | Lines |
| 57 | 44 | 361 | Angles + Lines |
| 43 | 17 | 511 | BMI |

Example 3

Automatic Compromised Cephalometric Analysis

This example describes an automated process for performing compromised cephalometric analysis.

SDB is associated with statistically significant changes in a number of cephalometric features such as anatomical airway narrowing or reduced mechanical stability of the tongue or the velopharynx [Finkelstein 2001 (supra)].

The term "compromised cephalometric parameters" (CCPs) is defined as a condition in which a cephalometric feature is more than one standard deviation from the mean in the direction of airway narrowing or increased airway instability. In various exemplary embodiments of the invention the list of parameters in the CCPs include at least one of: BASN, BaSPNS, GnGoH, MPH, Vw, RV-PAS and PPW. The following thresholds define, according to some embodiments of the present invention, compromised cephalometric parameters: BASN<128.2, BaSPNS<56.3, GnGoH>33.8, MPH>20.8, Vw>12, RV-PAS<6.2 and PPW>3.7.

Embodiments of the present invention has been used for analyzing 70 cephalometric images of patients with various degrees of CCPs. The images were the same images used in Example 2, above.

For each patient, the number of parameters that influence on the airway narrowing or instability was counted. The velopharyngeal parameters showed increased frequency of CCP status in the SDB group, with PPW and TDR being the most robust correlates of SDB severity.

Table 3 below provides a comparison between data presented in Finkelstein 2001 (supra) and the results of the automatic analysis of the present embodiments. The left column in Table 3 lists the number of CCPs, the second and third columns provides the control and test groups as measured manually by craniofacial complex experts and reported in Finkelstein 2001, and the rightmost column provides the results for the test group as obtained automatically according to some embodiments of the present invention.

TABLE 3

| Number | Manual | | Automatic |
|---|---|---|---|
| of CCPs | Control [%] | Test [%] | Test [%] |
| 0 | 24 | 0 | 0 |
| 1 | 24 | 1.25 | 0 |
| 2 | 21 | 6.50 | 2.5 |
| 3 | 24 | 10.25 | 6.5 |
| 4 | 5 | 24.50 | 23.5 |
| 5 | 2 | 27.25 | 29.5 |
| 6 | 0 | 20.75 | 29 |
| 7 | 0 | 6.25 | 9 |
| 8 | 0 | 0.00 | 0 |

Figure 13:
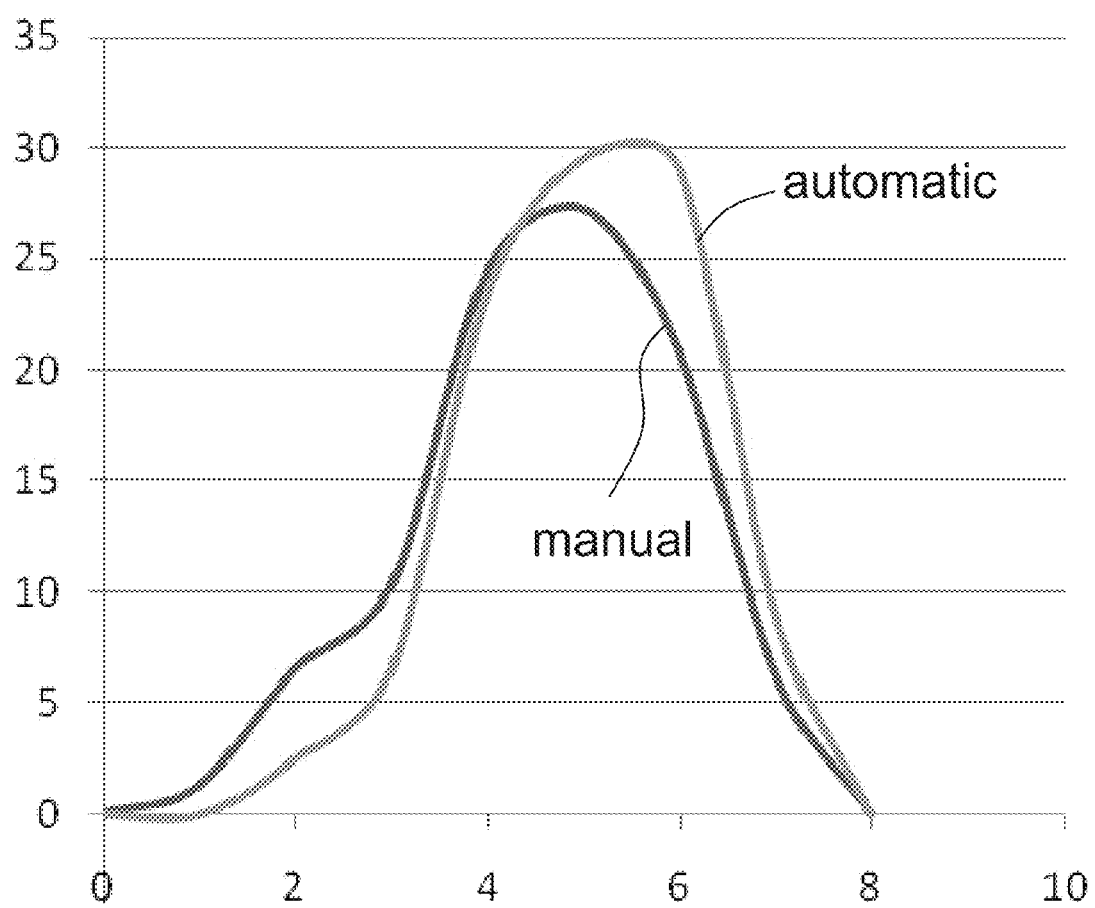
FIG. 13 is a graph comparing percentages of compromised cephalometric parameters (CCPs) measured manually by craniofacial complex experts, with CCPs obtained automatically according to some embodiments of the present invention.

FIG. 13 is a graph which compares the two rightmost columns of Table 3. FIG. 13 demonstrates that the technique of the present embodiment can automatically provide results which are similar to those obtained manually by craniofacial complex experts.

The RDI (hence also the severity of the SDB) was predicted via a linear Support Vector Regression model, and correlated to two cephalometric features: MPH and GoGnH. A linear regression revealed the correlation parameters listed in Table 4.

TABLE 4

| | coefficient | std. error | t-ratio |
|---|---|---|---|
| GoGnH | 0.539714 | 0.164664 | 3.278 |
| MPH | 0.318438 | 0.249146 | 1.278 |

The mean dependent variable was 38.3 with standard deviation of 22.1.

Example 4

Automated Extraction of Cephalometric Features From CT Images

The procedure described in Example 2 above has been utilized for several CT images.

FIG. 14 shows a registered and annotated image which was used as a database image in the present example. The image is a single slice of a sliced CT image of a male subject. The image was manually registered and annotated with the relevant anatomical landmarks by a cephalometric expert.

Figure 15:
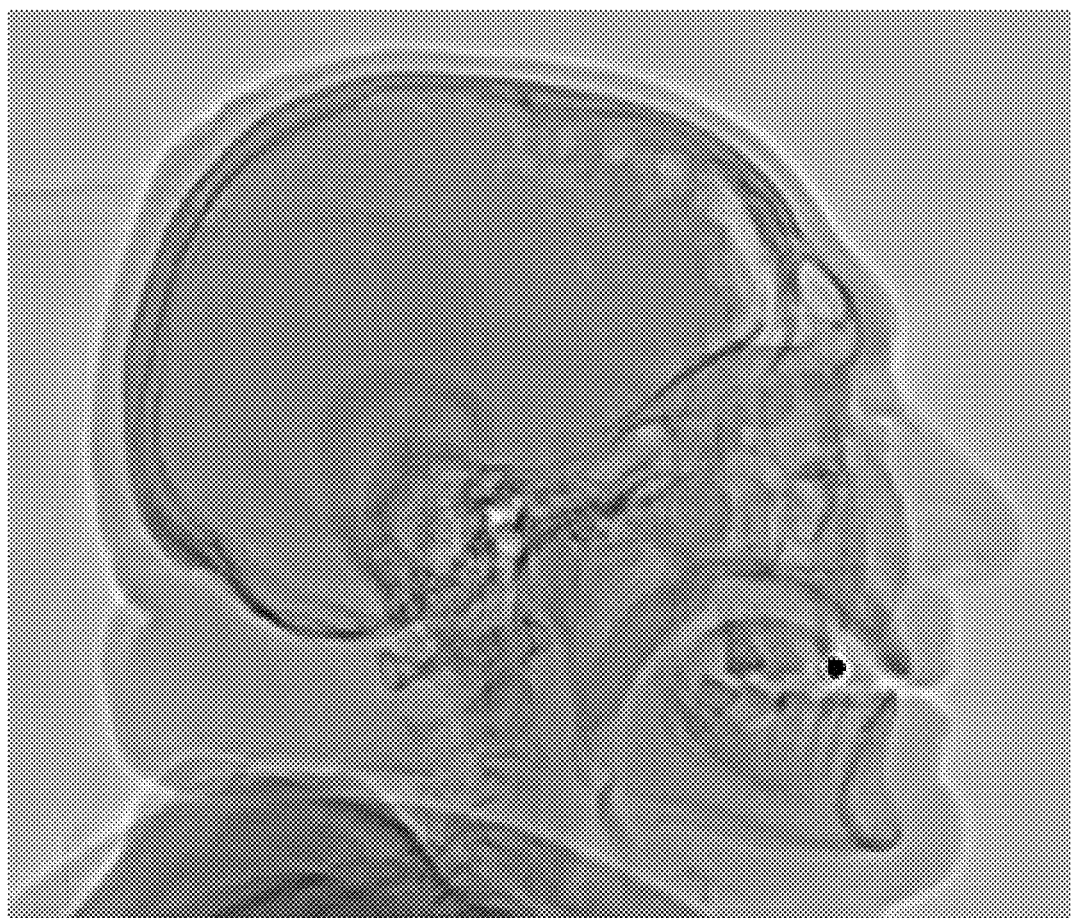
FIG. 15 shows a first target CT image which was analyzed according to some embodiments of the present invention.

FIG. 15 shows a first target image which was analyzed according to some embodiments of the present invention. This image is another single slice of the sliced CT image from which the slice shown in FIG. 14 was taken. Thus, FIGS. 14 and 15 are different slices of the same set, and therefore correspond to different projections (along different axes) of the same the craniofacial complex.

FIGS. 16A-B show a triplet matching between the database image (FIG. 16A) and the first target image (FIG. 16B), as obtained by employing the comparison procedure described in Example 2 above.

FIG. 17 shows the target image once the automatically detected points (red asterisks) were projected onto the image. Also shown, are the points as independently marked by the cephalometric expert (blue circles). As shown, the automatic projection coincides with the correct anatomical landmarks.

Similar results were obtained with three publicly available CT images, each being a single slice of a sliced CT image of a different subject. Thus, the present embodiments allow projecting anatomical landmarks base on comparison of a CT image of one craniofacial complex to a database CT image of another craniofacial complex.

Example 5

Automated Extraction of Cephalometric Features from MR Images

The procedure described in Example 2 above has been utilized for several MR images.

FIG. 18A shows a registered and annotated MR image which was used as a database image in the present example. The image is am MR image of a subject. The image was manually registered and annotated with the relevant anatomical landmarks by a cephalometric expert. FIG. 18B shows the same MR image, except without the annotation.

FIG. 19 shows a first target MR image which was analyzed according to some embodiments of the present invention. FIGS. 18A and 19 are different craniofacial complex MR images of different subjects.

FIGS. 20A-B show a triplet matching between the database MR image (FIG. 20A) and the first target MR image (FIG. 20B), as obtained by employing the comparison procedure described in Example 2 above.

FIGS. 21A-B show the first target MR image once the points (red asterisks) as automatically detected initially (FIG. 21A) and following an automatic fine-tuning procedure (FIG. 21B) were projected onto the image, as described in Example 2 above. Also shown, are the points as independently marked by the cephalometric expert (blue circles). As shown, the automatic projection coincides with the correct anatomical landmarks.

FIG. 22 shows a second target MR image which was analyzed according to some embodiments of the present invention. FIGS. 18A and 22 are different craniofacial complex MR images of different subjects.

FIGS. 23A-B show a triplet matching between the database MR image (FIG. 23A) and the second target MR image (FIG. 23B), as obtained by employing the comparison procedure described in Example 2 above.

FIGS. 24A-B show the second target MR image once the points (red asterisks) as automatically detected initially (FIG. 24A) and following an automatic fine-tuning procedure (FIG. 24B) were projected onto the image, as described in Example 2 above. Also shown, are the points as independently marked by the cephalometric expert (blue circles). As shown, the automatic projection coincides with the correct anatomical landmarks.

FIG. 25 shows a third target MR image which was analyzed according to some embodiments of the present invention. FIGS. 18A and 25 are different craniofacial complex MR images of different subjects.

FIGS. 26A-B show a triplet matching between the database MR image (FIG. 26A) and the third target MR image (FIG. 26B), as obtained by employing the comparison procedure described in Example 2 above.

FIGS. 27A-B show the third target MR image once the points (red asterisks) as automatically detected initially (FIG. 27A) and following an automatic fine-tuning procedure (FIG. 27B) were projected onto the image, as described in Example 2 above. Also shown, are the points as independently marked by the cephalometric expert (blue circles). As shown, the automatic projection coincides with the correct anatomical landmarks.

FIG. 28 shows a fourth target MR image which was analyzed according to some embodiments of the present invention. The fourth target MR has a lower resolution compared to the database image and the first to third target MR images. FIGS. 18A and 28 are different craniofacial complex MR images of different subjects.

FIGS. 29A-B show a triplet matching between the database MR image (FIG. 29A) and the fourth target MR image (FIG. 29B), as obtained by employing the comparison procedure described in Example 2 above.

FIG. 30 shows the fourth target MR image once the points (red asterisks) as automatically detected, following an automatic fine-tuning procedure, were projected onto the image, as described in Example 2 above. Also shown, are the points as independently marked by the cephalometric expert (blue circles). As shown, the automatic projection coincides with the correct anatomical landmarks, even for low resolution MR images.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method of analysis, comprising:
registering a target image to define a plurality of keypoints arranged in sets corresponding to polygons or linear segments in the target image, said registering comprising ordering keypoints of at least one set, according to descriptor vectors associated with said keypoints in said at least one set, so as to reduce an overall number of said sets, said ordering being by an ordering operator calculated by applying to said database a procedure for detecting keypoints together with associated information to provide a group of features, and projecting said descriptor vectors onto a first principal component of said group of features;
accessing a database of registered and annotated images, and employing a polygon-wise comparison between the target image and each database image; and
using said comparison for projecting annotated locations from said database images into the target image.

2. The method according to claim 1, wherein the target image is an image of a craniofacial complex of a subject, wherein said annotated locations correspond to cephalometric landmarks, and wherein the method further comprises extracting cephalometric features from the target image based on said annotated locations.

3. The method according to claim 2, further comprising repeating the analysis for an additional target image of said craniofacial complex of the same subject, wherein said target image and said additional target image correspond to different viewpoints.

4. The method according to claim 3, wherein said extracting said cephalometric features, comprises identifying three-dimensional cephalometric structures based on said different viewpoints.

5. The method according to claim 2, wherein said cephalometric features comprise angular relations between said cephalometric landmarks.

6. The method according to claim 5, wherein said angular relations comprise at least one angle selected from the group consisting of a skull base angle, a bony nasopharyngeal angle, a mandibular plane hyoid angle, and a skull base orientation angle between a the Basion-Pterygomaxillare line and the Basion-Sella line.

7. The method according to claim 2, wherein said extracting aid cephalometric features comprises modeling a shape of at least one cephalometric structure and fitting said model to annotated locations corresponding to said cephalometric structure in the target image.

8. The method according to claim 7, wherein said at least one cephalometric structure is the tongue, and said modeling comprises modeling said tongue as an ellipse.

9. The method according to claim 7, wherein said at least one cephalometric structure is the velum, and said modeling comprises modeling said velum using a basis spline.

10. The method according to claim 7, wherein said at least one cephalometric structure is the pharyngeal wall, and said modeling comprises modeling said pharyngeal wall as a straight line.

11. The method according to claim 2, further comprising assessing sleep disordered breathing (SDB) or the likelihood of SDB of the subject, based, at least in part, on said cephalometric features.

12. The method according to claim 2, further comprising calculating a respiratory disturbance index of the subject, based, at least in part, on said cephalometric features.

13. The method according to claim 2, further comprising calculating characteristic pharyngeal airflow resistance, based, at least in part, on said cephalometric features.

14. The method according to claim 2, wherein the target image is an image of said craniofacial complex of the subject without a dental device, and the method further comprises repeating the analysis for an additional target image of said craniofacial complex of the same subject with a dental device.

15. The method according to claim 14, further comprising comparing cephalometric features as extracted from the target image to cephalometric features as extracted from at least one additional target image, and using said comparison for assessing the effect of said dental device.

16. The method according to claim 1, wherein said target image is selected from the group consisting of an X-ray image, a Computerized Tomography (CT) image, and a Magnetic Resonance (MR) image, a thermal image, an ultraviolet image, a positron emission tomography (PET) image, an ultrasound image, an Electrical Impedance Tomography (EIT) image; a single photon emission computed tomography (SPECT) image, a sliced image and a three-dimensional image.

17. A system for analyzing an image, comprising:
an input circuit configured for receiving the image; and
a data processor configured for:
registering a target image to define a plurality of keypoints arranged in sets corresponding to polygons or linear segments in the target image, said registering comprising ordering keypoints of at least one set, according to descriptor vectors associated with said keypoints in said at least one set, so as to reduce an overall number of said sets, said ordering being by an ordering operator calculated by applying to said database a procedure for detecting keypoints together with associated information to provide a group of features, and projecting said descriptor vectors onto a first principal component of said group of features;
accessing a database of registered and annotated images, and employing a polygon-wise comparison between the image and each database image; and
using said comparison for projecting annotated locations from said database images into the image.

18. A computer software product, comprising a non-transitory computer-readable medium in which program instructions are stored, which instructions, when read by a data processor, cause the data processor to receive an image, register a target image to define a plurality of keypoints arranged in sets corresponding to polygons or linear segments in the target image, said registering comprising ordering keypoints of at least one set, according to descriptor vectors associated with said keypoints in said at least one set, so as to reduce an overall number of said sets, said ordering being by an ordering operator calculated by applying to said database a procedure for detecting keypoints together with associated information to provide a group of features, and projecting said descriptor vectors onto a first principal component of said group of features, access a database of registered and annotated images, and employ a polygon-wise comparison between said image and each database image, and use said comparison to project annotated locations from said database images into said image.

19. A method of analysis, comprising:
registering a target image to define a plurality of keypoints arranged in sets corresponding to polygons or linear segments in the target image, said registering comprising ordering keypoints of at least one set so as to reduce an overall number of said sets;
accessing a database of registered and annotated images, and employing a polygon-wise comparison between the target image and each database image; and
using said comparison for projecting annotated locations from said database images into the target image;
wherein the target image is an image of a craniofacial complex of a subject, wherein said annotated locations correspond to cephalometric landmarks, and wherein the method further comprises extracting cephalometric features from the target image based on said annotated locations;
wherein said extracting aid cephalometric features comprises modeling a shape of at least one cephalometric structure and fitting said model to annotated locations corresponding to said cephalometric structure in the target image; and
wherein said at least one cephalometric structure is the tongue, and said modeling comprises modeling said tongue as an ellipse.

20. A method of analysis, comprising:
registering a target image to define a plurality of keypoints arranged in sets corresponding to polygons or linear segments in the target image, said registering comprising ordering keypoints of at least one set so as to reduce an overall number of said sets;
accessing a database of registered and annotated images, and employing a polygon-wise comparison between the target image and each database image; and
using said comparison for projecting annotated locations from said database images into the target image;
wherein the target image is an image of a craniofacial complex of a subject, wherein said annotated locations correspond to cephalometric landmarks, and wherein the method further comprises extracting cephalometric features from the target image based on said annotated locations;
wherein said extracting aid cephalometric features comprises modeling a shape of at least one cephalometric structure and fitting said model to annotated locations corresponding to said cephalometric structure in the target image; and
wherein said at least one cephalometric structure is the velum, and said modeling comprises modeling said velum using a basis spline.

21. A method of analysis, comprising:
registering a target image to define a plurality of keypoints arranged in sets corresponding to polygons or linear segments in the target image, said registering comprising ordering keypoints of at least one set so as to reduce an overall number of said sets;
accessing a database of registered and annotated images, and employing a polygon-wise comparison between the target image and each database image; and
using said comparison for projecting annotated locations from said database images into the target image;
wherein the target image is an image of a craniofacial complex of a subject, wherein said annotated locations correspond to cephalometric landmarks, and wherein the method further comprises extracting cephalometric features from the target image based on said annotated locations;

wherein said extracting aid cephalometric features comprises modeling a shape of at least one cephalometric structure and fitting said model to annotated locations corresponding to said cephalometric structure in the target image;

wherein said at least one cephalometric structure is the pharyngeal wall, and said modeling comprises modeling said pharyngeal wall as a straight line.

22. A method of analysis, comprising:

registering a target image to define a plurality of keypoints arranged in sets corresponding to polygons or linear segments in the target image, said registering comprising ordering keypoints of at least one set so as to reduce an overall number of said sets;

accessing a database of registered and annotated images, and employing a polygon-wise comparison between the target image and each database image; and using said comparison for projecting annotated locations from said database images into the target image;

wherein the target image is an image of a craniofacial complex of a subject, wherein said annotated locations correspond to cephalometric landmarks, and wherein the method further comprises extracting cephalometric features from the target image based on said annotated locations; and wherein the method further comprises calculating characteristic pharyngeal airflow resistance, based, at least in part, on said cephalometric features.

* * * * *